(12) United States Patent
Sumino et al.

(10) Patent No.: US 7,642,368 B2
(45) Date of Patent: Jan. 5, 2010

(54) PROCESS FOR PRODUCING TRIARYLSULFONIUM SALT

(75) Inventors: Motoshige Sumino, Kawagoe (JP);
Kazuhito Fukasawa, Kawagoe (JP);
Shigeaki Imazeki, Kawagoe (JP);
Tetsuya Watanabe, Kawagoe (JP)

(73) Assignee: Wako Pure Chemical Industries, Ltd., Osaka (JP)

( * ) Notice: Subject to any disclaimer, the term of this patent is extended or adjusted under 35 U.S.C. 154(b) by 154 days.

(21) Appl. No.: 10/576,299

(22) PCT Filed: Oct. 4, 2004

(86) PCT No.: PCT/JP2004/014604
§ 371 (c)(1),
(2), (4) Date: Apr. 19, 2006

(87) PCT Pub. No.: WO2005/037778
PCT Pub. Date: Apr. 28, 2005

(65) Prior Publication Data
US 2007/0083060 A1     Apr. 12, 2007

(30) Foreign Application Priority Data
Oct. 21, 2003  (JP) .............................. 2003-360774

(51) Int. Cl.
*C07F 255/00*  (2006.01)

(52) U.S. Cl. .......................... 558/412; 568/58; 568/49; 568/45; 568/44

(58) Field of Classification Search .............. 430/270.1; 558/412; 568/68, 44, 45; 556/412
See application file for complete search history.

(56) References Cited

U.S. PATENT DOCUMENTS

| | | | | |
|---|---|---|---|---|
| 4,173,476 A * | 11/1979 | Smith et al. | .............. | 430/280.1 |
| 4,980,492 A * | 12/1990 | Dektar et al. | .............. | 556/64 |
| 5,569,784 A * | 10/1996 | Watanabe et al. | .............. | 564/430 |
| 5,633,409 A * | 5/1997 | Watanabe et al. | .............. | 568/49 |
| 5,705,702 A | 1/1998 | Osawa et al. | .............. | 568/77 |
| 5,824,824 A * | 10/1998 | Osawa et al. | .............. | 568/49 |
| 6,723,483 B1 * | 4/2004 | Oono et al. | .............. | 430/170 |
| 6,924,323 B2 * | 8/2005 | Ishihara et al. | .............. | 522/25 |
| 2003/0017425 A1 * | 1/2003 | Endo et al. | .............. | 430/322 |

FOREIGN PATENT DOCUMENTS

| | | |
|---|---|---|
| EP | 1 113 005 A1 | 7/2001 |
| JP | 9-12537 A | 1/1997 |
| JP | 3063615 B2 | 5/2000 |
| JP | 2001-122850 A | 5/2001 |

OTHER PUBLICATIONS

Wildi, Bernard S. et al., "The Preparation of Triarylsulfonium Halides by the Action of Aryl Grignard Reagents on Diphenyl Sulfoxide", *J. Am. Chem. Soc.*, vol. 73, 1951, pp. 1965-1967.
Dektar, John L. et al., "Photochemistry of Triarylsulfonium Salts", *J. Am. Chem. Soc.*, 1990, vol. 112, pp. 6004-6015.
Wiegand, Gayl H. et al., "Syntheses and Reactions of Triarylsulfonium Halides", *J. Org. Chem*, vol. 33, 1968, pp. 2671-2675.
Dougherty, Gregg et al., "A Synthesis of Aryl Sulfonium Salts", *J. Am. Chem. Soc.*, 1939, vol. 61, pp. 80-81.
Crivello, James V. et al., "A New Preparation of Triarylsulfonium and -selenonium Salts via the Copper(II)-Catalyzed Arylation of Sulfides and Selenides with Diaryliodonium Salts", *J. Org. Chem.*, vol. 43, 1978, pp. 3055-3059.
Andersen, Kenneth K. et al., "Synthesis of Triarylsulfonium Salts from Diarylethoxysulfonium Salts", *Tetrahedron Letters*, No. 45, pp. 5445-5449, 1966.
Imazeki, Shigeaki et al., "Facile Method for the Preparation of Triarylsulfonium Bromides Using Grignard Reagents and Chlorotrimethylsilane as an Activator", *Synthesis*, 2004, No. 10, pp. 1648-1654.

* cited by examiner

*Primary Examiner*—Sikarl A Witherspoon
*Assistant Examiner*—Chukwuma O Nwaonicha
(74) *Attorney, Agent, or Firm*—Kubovcik & Kubovcik

(57) ABSTRACT

A method for producing a triarylsulfonium salt having a structure that only one of the three arobatic rings of the three aromatic rings on the cationic portion is different from the other two aromatic groups, and which is useful, for example, as an acid-generating agent for a resist or a photo cationic polymerization initiator,

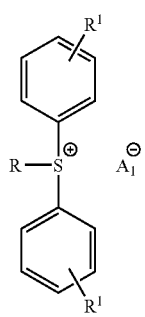

[4]

by reacting a diaryl sulfoxide

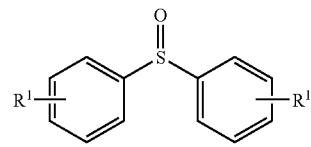

[1]

and an aryl Grignard reagent

RMgX   [2]

in the presence of an activator with high affinity for oxygen of 3 to 7.5 equivalents relative to the above diaryl sulfoxide, and then reacting the resultant reaction mixture with a strong acid

HA$_1$   [3].

9 Claims, No Drawings

US 7,642,368 B2

PROCESS FOR PRODUCING TRIARYLSULFONIUM SALT

This application is a 371 of international application PCT/JP2004/014604, which claims priority based on Japanese patent application No. 2003-360774 filed Oct. 21, 2003, which is incorporated herein by reference.

TECHNICAL FIELD

The present invention relates to a novel method for producing a triarylsulfonium salt useful as an acid-generating agent for a resist or a photo cationic polymerization initiator, having a structure that only one aromatic ring of three aromatic rings on the cationic portion thereof is different from the other two aromatic rings.

RELATED ARTS

A triarylsulfonium salt is broadly used as a photo acid-generating agent in a photolithography step in a field of semiconductor manufacturing.

These triarylsulfonium salts can be easily convertible into various counter anions via a triarylsulfonium halide (e.g. chloride, bromide, etc.) as an intermediate.

The known synthetic methods of triarylsulfonium bromide include, for example, (1) a method for reacting a diaryl sulfoxide and a Grignard reagent (see, e.g. non-patent literature 1, non-patent literature 2, etc.), (2) a method for condensing a diaryl sulfoxide and an aromatic hydrocarbon in the presence of aluminum chloride (see, e.g. non-patent literature 3), (3) a method for reacting a diaryl dichloro sulfide and an aromatic hydrocarbon in the presence of aluminum chloride (see, e.g. non-patent literature 4), and (4) a method for reacting a diaryl sulfide and a diaryl iodonium salt (see, e.g. non-patent literature 5).

These methods, however, have such problems as severe reaction conditions under high temperature (e.g. reflux operation by heating, melt reaction, etc.), generation of sulfurous acid gas and drainage of a large amount of aluminum waste liquid.

Therefore, a method for reacting a diaryl sulfoxide and an aryl Grignard reagent under a mild condition by coexisting with triethyloxonium tetrafluoroborate ($Et_3O.BF_4$) as an alkylating agent has been proposed (see, e.g. non-patent literature 6). However, $Et_3O.BF_4$ to be used in this method has problems that it is not only expensive but also an unstable compound and in addition is so harmful to human body that it is difficult to use and handle. It is not disclosed at all whether a sulfonium salt having a different structure on the cation portion is present or not as a byproduct in synthesizing an objective triarylsulfonium salt by this method.

To solve this problem, a method for synthesizing a triarylsulfonium salt by coexisting with chlorotrimethylsilane (TMSCl) as an activator instead of $Et_3O.BF_4$ has been proposed (see, e.g. patent literature 1). However, this method is suitable for synthesizing a sulfonium salt having three aromatic rings of the same structure on the cation portion, but has a problem that when this method is used as a method for introducing an aromatic ring having a different structure (structure b) from the aromatic rings of a diaryl sulfoxide [two aromatic rings thereof have the same structure (structure a)] into the above diaryl sulfoxide, obtained sulfonium salts having three aromatic rings include not only an objective compound (that is, a compound where two of three aromatic rings are of structure a, and another is of structure b), but also two kind of byproducts having different combinations of the aromatic rings (that is, a compound where all of three aromatic rings are of structure a, and/or a compound where one of three aromatic rings is of structure a, and the other two of them are of structure b).

Especially, when a triarylsulfonium salt is used as an acid-generating agent for a resist, coexisting byproducts are not suitable due to harmful effects on, for example, patterning, sensitivity, etc., which is difficult to be improved.

Under these situations, development of a method for effectively producing a triarylsulfonium salt having a structure that only one aromatic ring of three aromatic rings thereof is different, in a high yield without forming any byproduct, has been desired.

Patent Literature 1: JP-3163615

Non-patent Literature 1: B. S. Wildi, S. W. Taylor and H. A. portratz, Journal of the American Chemical Society, Vol. 73, p. 1965 (1951)

Non-patent Literature 2: J. L. Dektar and N. P. Hacker, Journal of the American Chemical Society, Vol. 112, No. 16, p. 6004 (1990)

Non-patent Literature 3: G. H. Wiegand and W. E. McEwen, The Journal of Organic Chemistry, Vol. 33, No. 7, p. 2671 (1968)

Non-patent Literature 4: G. Dougherty and P. D. Hammond, Journal of the American Chemical Society, Vol. 61, p. 80 (1939)

Non-patent Literature 5: J. V. Crivello and J. H. W. Lam, The Journal of Organic Chemistry, Vol. 43, No. 15, p. 3055 (1978)

Non-patent Literature 6: Kenneth K. Anderson and Nicholas E. Papanikolaou, Tetrahedron Letters, No. 45, p. 5445 (1966)

DESCRIPTION OF THE INVENTION

Problem to be Solved by the Present Invention

The present invention has been completed under such circumstances mentioned above, and the theme of the present invention is to provide a method for effectively producing a triarylsulfonium salt having a structure that only one aromatic ring of three aromatic rings on the cation portion thereof is different from the other two aromatic rings (hereinafter, abbreviated as a triarylsulfonium salt relating to the present invention) in a high yield without forming any byproducts.

Means to Solve the Problem

The present invention has been made to solve the above problem and is the invention of a method for producing a triarylsulfonium salt represented by the general formula [4]:

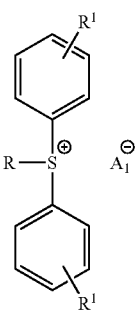

[4]

wherein, two R¹'s represent each hydrogen atom, halogen atom, alkyl group, haloalkyl group having 1 to 4 carbon atoms, alkoxy group, acyl group, hydroxyl group, amino group, nitro group or cyano group; R represents an aryl group which may have a substituent selected from a halogen atom, an alkyl group, a haloalkyl group having 1 to 4 carbon atoms, an alkoxy group, an alkylthio group, a N-alkylcarbamoyl group and a carbamoyl group, and the above substituent is different from one represented by the above R¹; and A₁ represents a strong acid residue, comprising reacting a diaryl sulfoxide represented by the general formula [1]:

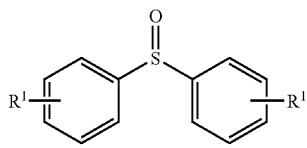

[1]

wherein, R¹ represents the same as above,
and an aryl Grignard reagent represented by the general formula [2]:

RMgX  [2]

wherein, X represents a halogen atom; R represents the same as above,
in the presence of an activator with high affinity for oxygen of 3 to 7.5 equivalents relative to the above diaryl sulfoxide, and then reacting the resultant reaction mixture with a strong acid represented by the general formula [3]:

HA₁  [3]

wherein, A₁ represents the same as above,
or a salt thereof.

Effect of the Invention

The method for producing a triarylsulfonium salt, of the present invention can produce a desired sulfonium salt to be efficiently in a high yield by using a larger amount of an activator with high affinity for oxygen than that conventionally used, without having such problems as severe reaction conditions under high temperature (e.g. reflux operation by heating, melt reaction, etc.), generation of sulfurous acid gas, drainage of a large amount of aluminum waste liquid, production of a sulfonium salt alone having the same three aromatic rings on the cation portion and formation of byproducts as impurities. Such effects are obtained by greatly increasing an amount of use of an activator with high affinity for an oxygen atom, which has not been predicted at all.

BEST MODE FOR CARRYING-OUT OF THE INVENTION

In general formula [1], the halogen atom represented by R¹ includes, for example, a fluorine atom, a chlorine atom, a bromine atom and an iodine atom.

The alkyl group represented by R¹ may be straight chained, branched or cyclic group, and includes one having generally 1 to 12 carbon atoms, preferably 1 to 6 carbon atoms, which is specifically exemplified by, for example, a methyl group, an ethyl group, a n-propyl group, an isopropyl group, a n-butyl group, an isobutyl group, a sec-butyl group, a tert-butyl group, a n-pentyl group, an isopentyl group, a sec-pentyl group, a tert-pentyl group, a neopentyl group, a 2-methylbutyl group, a 1-ethylpropyl group, a n-hexyl group, an isohexyl group, a sec-hexyl group, a tert-hexyl group, a neohexyl group, a 2-methylpentyl group, a 1,2-dimethylbutyl group, a 1-ethylbutyl group, a n-heptyl group, an isoheptyl group, a sec-heptyl group, a tert-heptyl group, a neoheptyl group, a n-octyl group, an isooctyl group, a sec-octyl group, a tert-octyl group, a neooctyl group, a n-nonyl group, an isononyl group, a sec-nonyl group, a tert-nonyl group, a neononyl group, a n-decyl group, an isodecyl group, a sec-decyl group, a tert-decyl group, a neodecyl group, a n-undecyl group, an isoundecyl group, a sec-undecyl group, a tert-undecyl group, a neoundecyl group, a n-dodecyl group, an isododecyl group, a sec-dodecyl group, a tert-dodecyl group, a neododecyl group, a cyclopropyl group, a cyclobutyl group, a cyclopentyl group, a cyclohexyl group, a cyclohexylmethyl group, a 2-cyclohexylethyl group, a cycloheptyl group, a cyclooctyl group, a cyclononyl group, a cyclodecyl group, a cycloundecyl group and a cyclododecyl group.

The haloalkyl group having 1 to 4 carbon atoms represented by R¹ includes one having generally 1 to 4 carbon atoms, preferably 1 to 2 carbon atoms wherein some or all of hydrogen atoms are hydroganated (e.g. fluorinated, chlorinated, brominated, iodinated, etc.), and may be straight chained, branched or cyclic group, which is specifically exemplified by, for example, a fluoromethyl group, a difluoromethyl group, a trifluoromethyl group, a chloromethyl group, a dichloromethyl group, a trichloromethyl group, a bromomethyl group, a dibromomethyl group, a tribromomethyl group, a iodomethyl group, a diiodomethyl group, a triiodomethyl group, a pentafluoroethyl group, a pentachloroethyl group, a pentaburomoethyl group, a pentaiodoethyl group, a heptafluoropropyl group, a heptachloropropyl group, a heptabromopropyl group, a heptaiodopropyl group a nonafluorobutyl group, a nonachlorobutyl group, a nonabromobutyl group and a nonaiodobutyl group.

The alkoxy group represented by R¹ may be straight chained, branched or cyclic group, and includes one having generally 1 to 8 carbon atoms, preferably 1 to 6 carbon atoms, which is specifically exemplified by, for example, a methoxy group, an ethoxy group, a n-propoxy group, an isopropoxy group, a n-butoxy group, an isobutoxy group, a sec-butoxy group, a tert-butoxy group, a n-pentyloxy group, an isopentyloxy group, a sec-pentyloxy group, a tert-pentyloxy group, a neopentyloxy group, a n-hexyloxy group, an isohexyloxy group, a sec-hexyloxy group, a tert-hexyloxy group, a neohexyloxy group, a n-heptyloxy group, an isoheptyloxy group, a sec-heptyloxy group, a tert-heptyloxy group, a neoheptyloxy group, a n-octyloxy group, an isooctyloxy group, a sec-octyloxy group, a tert-octyloxy group, a neopentyloxy group, a cyclopropoxy group, a cyclobutoxy group, a cyclopentyloxy group, a cyclohexyloxy group, a cycloheptyloxy group and a cyclooctyloxy group.

The acyl group represented by R¹ includes one derived from carboxylic acid having generally 1 to 16 carbon atoms, which is specifically exemplified by, for example, a group derived from aliphatic carboxylic acids such as a formyl group, an acetyl group, a propionyl group, a butyryl group, an isobutyryl group, a valeryl group, an isovaleryl group, a pivaroyl group, a hexanoyl group, a heptanoyl group, an octanoyl group, a nonanoyl group, a decanoyl group, an undecanoyl group, a lauroyl group, a myristoyl group, a palmitoyl group and a cyclohexylcarbonyl group; and a group derived from aromatic carboxylic acids such as an benzoyl group, a naphthoyl group and a toluoyl group.

In the general formula [2], the aryl group of the aryl group represented by R, which may have a substitutent selected from a halogen atom, an alkyl group, an haloalkyl group having 1 to 4 carbon atoms, an alkoxy group, an alkylthio group, a N-alkylcarbamoyl group, a carbamoyl group includes one generally having 6 to 14 carbon atoms, preferable 6 to 10 carbon atoms, which is specifically exemplified by, for example, a phenyl group, a naphthyl group, an anthryl group and a phenanthryl group.

The aryl group represented by R may have a substituent selected from a halogen atom, an alkyl group, a haloalkyl group having 1 to 4 carbon atoms, an alkoxy group, an alkylthio group, a N-alkylcarbamoyl group, or a carbamoyl group. Among them, the halogen atom, the alkyl group, the haloalkyl group having 1 to 4 carbon atoms, or the alkoxy group, as the substituent is the same one exemplified as the substituent represented by $R^1$ in the general formula [1].

The alkylthio group exemplified as the substituent of the aryl group represented by R, which may have one selected from a halogen atom, an alkyl group, an haloalkyl group having 1 to 4 carbon atoms, an alkoxy group, an alkylthio group, N-alkylcarbamoyl group, or a carbamoyl group includes one wherein oxygen atom of alkoxy group is replaced by sulfur atom, and may be straight chained, branched, or cyclic group. The specific example of such a group includes, for example, a methylthio group, an ethylthio group, a n-propylthio group, an isopropylthio group, a n-butylthio group, an isobutylthio group, a sec-butylthio group, a tert-butylthio group, a n-pentylthio group, an isopentylthio group, a sec-pentylthio group, a tert-pentylthio group, a neopentylthio group, a 2-methylbutylthio group, a 1-ethylpropylthio group, a n-hexylthio group, an isohexylthio group, a sec-hexylthio group, a tert-hexylthio group, a neohexylthio group, a 2-methylpentylthio group, a 3-methylpentylthio group, a 1,2-dimethylbutylthio group, a 2,2-dimethylbutylthio group, a 1-ethylbutylthio group, a 2-ethylbutylthio group, a n-heptylthio group, an isoheptylthio group, a sec-heptylthio group, a tert-heptylthio group, a neoheptylthio group a n-octylthio group, an isooctylthio group, a sec-octylthio group, a tert-octylthio group, a neooctylthio group, a cyclopropylthio group, a cyclobutylthio group, a cyclopentylthio group, a cyclohexylthio group, a cycloheptylthio group and a cyclooctylthio group.

The N-alkylcarbamoyl group exemplified as one of a substituent of the aryl group represented by R, which may have a group selected from a halogen atom, an alkyl group, an haloalkyl group having 1 to 4 carbon atoms, an alkoxy group, an alkylthio group, a N-alkylcarbamoyl group, or a carbamoyl group includes one wherein some hydrogen atoms of carbamoyl group are replaced by alkyl groups having 1 to 6 carbon atoms. The specific example of such a group includes, for example, a N-methylcarbamoyl group, a N-ethylcarbamoyl group, a N-n-propylcarbamoyl group, a N-isopropylcarbamoyl group, a N-n-butylcarbamoyl group, a N-isobutylcarbamoyl group, a N-tert-butylcarbamoyl group, a N-n-pentylcarbamoyl group, a N-isopentylcarbamoyl group, a N-tert-pentylcarbamoyl group, a N-n-hexylcarbamoyl group, a N-isohexylcarbamoyl group and a N-tert-hexylcarbamoyl group.

The halogen atom represented by X includes, for example, a fluorine atom, a chlorine atom, a bromine atom and iodine atom, among them, for example, fluorine atom or chlorine atom is preferable, and in particular, fluorine atom is more preferable.

Furthermore, substituents represented by $R^1$ in the general formula [1] differ from ones of the aryl group which may have substituents, represented by R in the general formula [2]. Either the following partial structure in the general formula [1]:

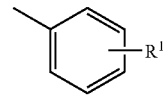

or R in the general formula [2] may be a phenyl group.

In the general formula [3], the strong acid residue represented by $A_1$ includes one derived from hydrohalic acid in the general formula [5]:

 [5]

(wherein $X_1$ represents a halogen atom); a sulfonic acid in the general formula [6]:

 [6]

(wherein $R^2$ represents an alkyl group, an aryl group, an aralkyl group, which may have halogen atom, or camphor group); and an inorganic strong acid in the general formula [7]:

 [7]

(wherein $M_1$ represents a metalloid metal and n is an integer of 4 or 6).

In the general formula [5], the halogen atom represented by $X_1$ includes, for example, a fluorine atom, a chlorine atom, a bromine atom and an iodine atom, and among others, a chlorine atom or a bromine atom is preferable. In particular, a bromine atom is more preferable.

In the general formula [6], the alkyl group of the alkyl group which may have halogen atoms, represented by $R^2$ may be straight chained, branched or cyclic group, and includes one having generally 1 to 29 carbon atoms, preferably 1 to 18 carbon atoms, more preferably 1 to 8 carbon atoms, which is specifically exemplified by, for example, a methyl group, an ethyl group, a n-propyl group, an isopropyl group, a n-butyl group, an isobutyl group, a sec-butyl group, a tert-butyl group, a n-pentyl group, an isopentyl group, a sec-pentyl group, a tert-pentyl group, a neopentyl group, a n-hexyl group, an isohexyl group a sec-hexyl group, a tert-hexyl group, a neohexyl group a n-heptyl group, an isoheptyl group, a sec-heptyl group, a tert-heptyl group a neoheptyl group a n-octyl group, an isooctyl group, a sec-octyl group, a tert-octyl group, a neooctyl group, a n-nonyl group, an isononyl group, a sec-nonyl group, a tert-nonyl group, a neononyl group, a n-decyl group, an isodecyl group, a sec-decyl group, a tert-decyl group, a neodecyl group, a n-undecyl group, an isoundecyl group, a sec-undecyl group, a tert-undecyl group, a neoundecyl group, a n-dodecyl group, an isododecyl group, a sec-dodecyl group, a tert-dodecyl group, a neododecyl group, a n-tridecyl group, an isotridecyl group, a sec-tridecyl group, a tert-tridecyl group, a neotridecyl group, a n-tetradecyl group, an isotetradecyl group, a sec-tetradecyl group, a tert-tetradecyl group, a neotetradecyl group, a n-pentadecyl group, an isopentadecyl group, a sec-pentadecyl group, a tert-pentadecyl group, a neopentadecyl group, a n-hexadecyl group, an isohexadecyl group, a sec-hexadecyl group, a tert-hexadecyl group, a neohexadecyl group, a n-heptadecyl group, an isoheptadecyl group, a sec-heptadecyl group, a tert-heptadecyl group, a neoheptadecyl group, a n-octadecyl group, an isooctadecyl group, a sec-octadecyl group, a tert-octadecyl group, a neooctadecyl group, a n-nonadecyl group, an isononadecyl group, a sec-nonadecyl group, a tert-nonadecyl group, a neononadecyl group, a n-icosyl group, an isoicosyl group, a sec-icosyl group, a tert-icosyl group, a neoicosyl group, a n-henicosyl group, an isohenicosyl group, a sec-henicosyl group, a tert-henicosyl group, a neoicosyl group, a n-docosyl group, an isodocosyl group, a sec-docosyl group, a tert-docosyl group, a neodocosyl group, a n-tricosyl group, an isotricosyl group, a sec-tricosyl group, a tert-tricosyl group, a neotricosyl group, a n-tetracosyl group, an isotetracosyl group, a sec-tetracosyl group, a tert-tetracosyl group, a neotetracosyl group, a n-pentacosyl group, an isopentacosyl group, a sec-pentacosyl group, a tert-pentacosyl group, a neopentacosyl group, a n-hexacosyl group, an isohexacosyl group, a sec-hexacosyl group, a tert-hexacosyl group, a neohexacosyl group, a n-heptacosyl group, an isoheptacosyl group a sec-heptacosyl group, a tert-heptacosyl group, a neoheptacosyl group, a n-octacosyl group, an isooctacosyl group, a sec-octacosyl group, a tert-octacosyl group, a neooctacosyl group, a n-nonacosyl group, an isononacosyl group, sec-nonacosyl group, a tert-nonacosyl group, a neononacosyl group, a cyclopropyl group, a cyclobutyl group, a cyclopentyl group, a cyclohexyl group, a cyclooctyl group, a cyclononyl group, a cyclodecyl group, a cycloundecyl group, a cyclododecyl group, a cyclotridecyl group, a cyclotetradecyl group, a cyclopentadecyl group, a cyclohexadecyl group, a cycloheptadecyl group, a cyclooctadecyl group, a cyclononadecyl group, a cycloicosyl group a cyclohenicosyl group, a cyclodocosyl group, a cyclotricosyl group, a cyclotetracosyl group, a cyclopentacosyl group, a cyclohexacosyl group, a cycloheptacosyl group, a cyclooctacosyl group and a cyclononacosyl group.

The aryl group of the aryl group which may have halogen atoms, represented by $R^2$ includes one having generally 6 to 16 carbon atoms, preferably 6 to 14 carbon atoms, which is specifically exemplified by, for example, a phenyl group, a naphthyl group, an anthryl group, a phenanthryl group and a pyrenyl group.

The aralkyl group of an aralkyl group which may have halogen atoms, represented by $R^2$ includes one having generally 7 to 15 carbon atoms, preferably 7 to 10 carbon atoms, which is specifically exemplified by, for example, a benzyl group, a phenethyl group, a phenylpropyl group, a phenylbutyl group, 1-methyl-3-phenylpropyl group, a phenylpentyl group, a phenylhexyl, group, a phenylheptyl group, a phenyloctyl group and a phenylnonyl group.

The alkyl group, the aryl group and the aralkyl group, which may have a halogen atom, represented by $R^2$ includes one wherein some or all of hydrogen atoms of the above alkyl, aryl and aralkyl group are replaced by halogen atoms (e.g. a fluorine atom, a chlorine atom, a bromine atom, an iodine atom, etc.).

Specifically, in the alkyl group, it is preferable that one, wherein all hydrogen atoms, or generally 1 to 30 hydrogen atoms, preferably 1 to 16 hydrogen atoms thereof are substituted by a halogen atom, and among others, one wherein all hydrogen atoms are substituted by a halogen atom is preferable.

Specifically, in the aryl group, it is preferable that one, wherein 1 to 5 hydrogen atoms, preferably 3 to 5 hydrogen atoms in the ring thereof are substituted by a halogen atom, and among others, one wherein all hydrogen atoms in the ring thereof are substituted by a halogen atom is preferable.

Specifically, in the aralkyl group, it is preferable that one, wherein hydrogen atoms in the alkyl group moiety and/or aryl group moiety are substituted by a halogen atom, and includes one wherein all or a part of hydrogen atoms in the alkyl group moiety thereof are substituted by a halogen atom, and 1 to 5 hydrogen atoms, preferably 5 hydrogen atoms in the aryl ring thereof are substituted by a halogen atom.

An alkyl group, an aryl group or an aralkyl group, which may have halogen atoms, represented by $R^2$, may further have a substituent other than said halogen atom and said substituent includes, for example, an alkyl group having 1 to 4 carbon atoms such as a methyl group, an ethyl group, a n-propyl group, an isopropyl group, a n-butyl group, an isobutyl group, a sec-butyl group and a tert-butyl group; a haloalkyl group having 1 to 4 carbon atoms such as a fluoromethyl group, a difluoromethyl group, a trifluoromethyl group, a chloromethyl group, a dichloromethyl group, a trichloromethyl group, a bromomethyl group, a dibromomethyl group, a tribromomethyl group, a iodomethyl group, a diiodomethyl group, a triiodomethyl group, a trifluoroethyl group, a trichloroethyl group, a tribromoethyl group, a triiodoethyl group, a pentafluoroethyl group, a pentachloroethyl group, a pentabromoethyl group, a pentaiodoethyl group, a heptafluoropropyl group, a heptachloropropyl group, a heptabromopropyl group, a heptaiodopropyl group, a nonafluorobutyl group, a nonachlorobutyl group, a nonabromobutyl group and a non-aiodobutyl group; an alkoxy group having 1 to 4 carbon atoms such as a methoxy group, an ethoxy group, a n-propoxy group, an isopropoxy group, a n-butoxy group, an isobutoxy group, a sec-butoxy group and a tert-butoxy group.

In the general formula [7], the metalloid metal represented by $M_1$ includes, for example, a boron atom, a silicon atom, a phosphorus atom, an arsenic atom and an antimony atom. Among them, a boron atom, a phosphorus atom, an arsenic atom, or an antimony atom is preferable, and in particular, a boron atom or a phosphorus atom is more preferable.

The activating agent having high oxygen affinity to be used in this invention includes, for example, halogenotriorganosilane, triorganophosphine and triorganophosphate, which is specifically exemplified by, for example, halogenotrialkylsilanes such as chlorotrimethylsilane, chlorotriethylsilane, chlorodimethylcyclohexylsilane, chloroisopropyldimethylsilane, chlorodimethyl-tert-butylsilane, chlorodimethyl(2,3-dimethylbutyl)silane, chlorotrisopropylsilane and bromotrimethylsilane; halogenotriorganosilanes such as chlorodimethylphenylsilane; triorganophosphines such as triphenylphosphine, tri-n-butylphosphine, tri-n-hexylphosphine, tri-n-octylphosphine, tricyclohexylphosphine, diethylphenylphosphine, dicyclohexylphenylphosphine, methyldiphenylphosphine, ethyldiphenylphosphine, diphenyl-n-propylphosphine, isopropyldiphenylphosphine, tri(2-methylphenyl)phosphino and tri(3-methylphenyl)phosphine; triorgano phosphates such as trimethyl phosphate, triethyl phosphate, tri-n-butyl phosphate, tri-n-amyl phosphate, tri-n-octyl phosphate, triphenyl phosphate and tritolyl phosphate. Among them, halogenotrialkylsilane is preferable, and in particular, chlorotrimethylsilane is more preferable.

The preferable examples of the diaryl sulfoxide represented in the general formula [1] include, for example, diphenylsulfoxide, bis(4-methylphenyl)sulfoxide, bis(3-methylphenyl)sulfoxide, bis(2-methylphenyl)sulfoxide, bis(4-methoxyphenyl)sulfoxide, bis(2-methoxyphenyl)sulfoxide, bis(2-methoxyphenyl)sulfoxide, bis(4-tert-butylphenyl)sulfoxide, bis(4-trifluoromethylphenyl)sulfoxide, bis(4-fluorophenyl)sulfoxide, bis(4-chlorophenyl)sulfoxide and dinaphthylsulfoxide, bis(hydroxyphenyl)sulfoxide.

The preferable examples of the aryl Grignard reagents represented in the general formula [2] include, for example, phenyl-magnesium bromide, 4-methylphenylmagnesium bromide, 3-methylphenylmagnesium bromide, 2-methylphenylmagnesium bromide, 4-tert-butylphenylmagnesium bromide, 4-cyclohexylphenylmagnesium bromide, 4-methoxyphenylmagnesium bromide, 3-methoxyphenylmagnesium bromide, 4-n-butoxyphenylmagnesium bromide, 2-n-butoxyphenylmagnesium bromide, 4-tert-butoxyphenylmagnesium bromide, 4-cyclohexyloxyphenylmagnesium bromide, 4-methylthiophenylmagnesium bromide, 2,4,6-trimethylphenylmagnesium bromide, 3,5-dimethyl-4-methoxyphenylmagnesium bromide; 4-fluorophenylmagnesium bromide, 4-chlorophenylmagnesium bromide, 4-trifluoromethylphenylmagnesium bromide, naphthylmagnesium bromide, phenylmagnesium chloride, 4-methylphenylmagnesium chloride, 3-methylphenylmagnesium chloride, 2-methylphenylmagnesium chloride, 4-tert-butylphenylmagnesium chloride, 4-cyclohexylphenylmagnesium chloride, 4-methoxyphenylmagnesium chloride, 3-methoxyphenylmagnesium chloride, 4-n-butoxyphenylmagnesium chloride, 2-n-butoxyphenylmagnesium chloride, 4-tert-butoxyphenylmagnesium chloride, 4-cyclohexyloxyphenylnagnesium chloride, 4-methylthiophenylmagnesium chloride, 2,4,6-trimethylphenylmagnesium chloride, 3,5-dimethyl-4-methoxyphenylmagnesium chloride, 4-fluorophenylmagnesium chloride, 4-chlorophenylmagnesium chloride, 4-trifluoromethylphenylmagnesium chloride and naphthylmagnesium chloride.

The preferable examples of the hydrohalic acid represented by the general formula [5] or a salt thereof, include, for example, hydrofluoric acid, hydrochloric acid, hydrobromic acid, hydroiodic acid or a salt thereof (e.g. lithium salt, sodium salt, potassium salt, rubidium salt, silver salt, cesium salt, etc.). Among them, hydrochloric acid or hydrobromic acid is preferable, and in particular, hydrobromic acid is more preferable.

The preferable examples of the sulfonic acid represented by the general formula [6] or a salt thereof, include, for example, alkylsulfonic acids such as methanesulfonic acid, ethanesulfonic acid, propanesulfonic acid, butanesulfonic acid, pentanesulfonic acid, hexanesulfonic acid, heptanesulfonic acid, octanesulfonic acid, nonanesulfonic acid, decanesulfonic acid, undecanesulfonic acid, dodecanesulfonic acid, tridecanesulfonic acid, tetradecanesulfonic acid, pentadecanesulfonic acid, hexadecanesulfonic acid, heptadecanesulfonic acid, octadecanesulfonic acid, nonadecanesulfonic acid, icosanesulfonic acid, henicosanesulfonic acid, docosanesulfonic acid, tricosanesulfonic acid and tetracosanesulfonic acid; haloalkyl sulfonic acids such as fluoromethane sulfonic acid, difluoromethanesulfonic acid, trifluoromethanesulfonic acid, chloromethanesulfonic acid, dichloromethanesulfonic acid, trichloromethanesulfonic acid, bromomethanesulfonic acid, dibromomethanesulfonic acid, tribromomethanesulfonic acid, iodomethanesulfonic acid, diiodomethanesulfonic acid, triiodomethanesulfonic acid, fluoroethanesulfonic acid, difluoroethanesulfonic acid, trifluoroethanesulfonic acid, pentafluoroethanesulfonic acid, chloroethanesulfonic acid, dichloroethanesulfonic acid, trichloroethanesulfonic acid, pentachlorethanesulfonic acid, tribromoethanesulfonic acid, pentabromoethanesulfonic acid, triiodoethanesulfonic acid, pentaiodoethanesulfonic acid, fluoropropanesulfonic acid, trifluoropropanesulfonic acid, heptafluoropropanesulfonic acid, chloropropanesulfonic acid, trichloropropanesulfonic acid, heptachloropropanesulfonic acid, bromopropanesulfonic acid, tribromopropanesulfonic acid, heptabromopropanesulfonic acid, triiodopropanesulfonic acid, heptaiodopropanesulfonic acid, trifluorobutanesulfonic acid, nonafluorobutanesulfonic acid, trichlorobutanesulfonic acid, nonachlorobutanesulfonic acid, tribromobutanesulfonic acid, nonabromobutanesulfonic acid, triiodobutanesulfonic acid, nonaiodobutanesulfonic acid, trifluoropentanesulfonic acid, perfluoropentanesulfonic acid, trichloropentanesulfonic acid, perchloropentanesulfonic acid, tribromopentanesulfonic acid, perbromopentanesulfonic acid, triiodopentanesulfonic acid, periodopentanesulfonic acid, trifluorohexanesulfonic acid, perfluorohexanesulfonic acid, trichlorohexanesulfonic acid, perchlorohexanesulfonic acid, perbromohexanesulfonic acid, periodohexanesulfonic acid, trifluoroheptanesulfonic acid, perfluoroheptanesulfonic acid, trichloroheptanesulfonic acid, perchloroheptanesulfonic acid, perbromoheptanesulfonic acid, periodoheptanesulfonic acid, trifluorooctanesulfonic acid, perfluorooctanesulfonic acid, trichlorooctanesulfonic acid, perchlorooctanesulfonic acid, perbromooctanesulfonic acid, periodooctanesulfonic acid, trifluorononanesulfonic acid, perfluorononanesulfonic acid, trichlorononanesulfonic acid, perchlorononanesulfonic acid, perbromononanesulfonic acid, periodononanesulfonic acid, trifluorodecanesulfonic acid, perfluorodecanesulfonic acid, trichlorodecanesulfonic acid, perchlorodecanesulfonic acid, perbromodecanesulfonic acid, periododecanesulfonic acid, trifluoroundecanesulfonic acid, perfluoroundecanesulfonic acid, trichloroundecanesulfonic acid, perchloroundecanesulfonic acid, perbromoundecanesulfonic acid, periodoundecanesulfonic acid, trifluorododecanesulfonic acid, perfluorododecanesulfonic acid, trichlorododecanesulfonic acid, perchlorododecanesulfonic acid, perbromododecanesulfonic acid, periodododecanesulfonic acid, trifluorotridecanesulfonic acid, perfluorotridecanesulfonic acid, trichlorotridecanesulfonic acid, perchlorotridecanesulfonic acid, perbromotridecanesulfonic acid, periodotridecanesulfonic acid, trifluorotetradecanesulfonic acid, perfluorotetradecanesulfonic acid, trichlorotetradecanesulfonic acid, perchlorotetradecanesulfonic acid, perbromotetradecanesulfonic acid, periodotetradecanesulfonic acid, trifluoropentadecanesulfonic acid, perfluoropentadecanesulfonic acid, trichloropentadecanesulfonic acid, perchloropentadecanesulfonic acid, perbromopentadecanesulfonic acid, periodopentadecanesulfonic acid, perfluorohexadecanesulfonic acid, perchlorohexadecanesulfonic acid, perbromohexadecanesulfonic acid, periodohexadecanesulfonic acid, perfluoroheptadecanesulfonic acid, perchloroheptadecanesulfonic acid, perbromoheptadecanesulfonic acid, periodoheptadecanesulfonic acid, perfluorooctadecanesulfonic acid, perchlorooctadecanesulfonic acid, perbromooctadecanesulfonic acid, periodooctadecanesulfonic acid, perfluorononadecanesulfonic acid, perchlorononadecanesulfonic acid, perbromononadecanesulfonic acid, periodononadecanesulfonic acid, perfluoroicosanesulfonic acid, perchloroicosanesulfonic acid, perbromoicosanesulfonic acid, periodoicosanesulfonic acid, perfluorohenicosanesulfonic acid, perchlorohenicosanesulfonic acid, perbromohenicosanesulfonic acid, periodohenicosanesulfonic acid, perfluorodocosanesulfonic acid, perchlorodocosanesulfonic acid, perbromodocosanesulfonic acid, periododocosanesulfonic acid, perfluorotricosanesulfonic acid, perchlorotricosanesulfonic acid, perbromotricosanesulfonic acid, periodotricosanesulfonic acid, perfluorotetracosanesulfonic acid, perchlorotetracosanesulfonic acid, perbromotetracosanesulfonic acid and periodotetracosanesulfonic acid; cycloalkyl sulfonic acids such as cyclopentanesulfonic acid and cyclohexanesulfonic acid; halogenated cycloalkylsulfonic acids such as 2-fluorocyclopentanesulfonic acid, 2-chlorocyclopentanesulfonic acid, 2-bromocyclopentanesulfonic acid, 2-iodocyclopentanesulfonic acid, 3-fluorocyclopentanesulfonic acid, 3-chlorocyclopentanesulfonic acid, 3-bromocyclopentanesulfonic acid, 3-iodocyclopentanesulfonic acid, 3,4-difluorocyclopentanesulfonic acid, 3,4-dichlorocyclopentanesulfonic acid, 3,4-dibromocyclopentanesulfonic acid, 3,4-diiodocyclopentanesulfonic acid, 4-fluorocyclohexanesulfonic acid, 4-chlorocyclohexanesulfonic acid, 4-bromocyclohexanesulfonic acid, 4-iodocyclohexanesulfonic acid, 2,4-difluorocyclohexanesulfonic acid, 2,4-dichlorocyclohexanesulfonic acid, 2,4-dibromocyclohexanesulfonic acid, 2,4-diiodocyclohexanesulfonic acid, 2,4,6-trifluorocyclohexanesulfonic acid, 2,4,6-trichlorocyclohexanesulfonic acid, 2,4,6-tribromocyclohexanesulfonic acid, 2,4,6-triiodocyclohexanesulfonic acid, tetrafluorocyclohexanesulfonic acid, tetrachlorocyclohexanesulfonic acid, tetrabromocyclohexanesulfonic acid and tetraiodocyclohexanesulfonic acid; aromatic sulfonic acids such as benzenesulfonic acid, naphthalenesulfonic acid, anthracenesulfonic acid, phenanthrenesulfonic acid and pyrenesulfonic acid; halogenated aromatic sulfonic acids such as 2-fluorobenzenesulfonic acid, 3-fluorobenzenesulfonic acid, 4-fluorobenzenesulfonic acid, 2-chlorobenzenesulfonic acid, 3-chlorobenzenesulfonic acid, 4-chlorobenzenesulfonic acid, 2-bromobenzenesulfonic acid, 3-bromobenzenesulfonic acid, 4-bromobenzenesulfonic acid, 2-iodobenzenesulfonic acid, 4-iodobenzenesulfonic acid, 2,4-difluorobenzenesulfonic acid, 2,6-difluorobenzenesulfonic acid, 2,4-dichlorobenzenesulfonic acid, 2,6-dichlorobenzenesulfonic acid, 2,4-dibromobenzenesulfonic acid, 2,6-dibromobenzenesulfonic acid, 2,4-diiodobenzenesulfonic acid, 2,6-diiodobenzenesulfonic acid, 2,4,6-trifluorobenzenesulfonic acid, 3,4,5-trifluorobenzenesulfonic acid, 2,4,6-trichlorobenzenesulfonic acid, 3,4,5-trichlorobenzenesulfonic acid, 2,4,6-tribromobenzenesulfonic acid, 3,4,5-tribromobenzenesulfonic acid, 2,4,6-triiodobenzenesulfonic acid, 3,4,5-triiodobenzenesulfonic acid, pentafluorobenzenesulfonic acid, pentachlorobenzenesulfonic acid, pentabromobenzenesulfonic acid, pentaiodobenzenesulfonic acid, fluoronaphthalenesulfonic acid, chloronaphthalenesulfonic acid, bromonaphthalenesulfonic acid, iodonaphthalenesulfonic acid, fluoroanthracenesulfonic acid, chloroanthracenesulfonic acid, bromoanthracenesulfonic acid and iodoanthracenesulfonic acid; alkylaromatic sulfonic acids such as p-toluenesulfonic acid, 4-isopropylbenzenesulfonic acid, 3,5-bis(trimethyl)benzenesulfonic acid, 3,5-bis(isopropyl)benzenesulfonic acid, 2,4,6-tris(trimethyl)benzenesulfonic acid and 2,4,6-tris(isopropyl) benzenesulfonic acid; halogenatedalkylaromatic sulfonic acids such as 2-trifluoromethylbenzenesulfonic acid, 2-trichloromethylbenzenesulfonic acid, 2-tribromomethylbenzenesulfonic acid, 2-triiodomethylbenzenesulfonic acid, 3-trifluoromethylbenzenesulfonic acid, 3-trichloromethylbenzenesulfonic acid, 3-tribromomethylbenzenesulfonic acid, 3-triiodomethylbenzenesulfonic acid, 4-trifluoromethylbenzenesulfonic acid, 4-trichloromethylbenzenesulfonic acid, 4-tribromomethylbenzenesulfonic acid, 4-triiodomethylbenzenesulfonic acid, 2,6-bis(trifluoromethyl)benzenesulfonic acid, 2,6-bis(trichloromethyl)benzenesulfonic acid, 2,6-bis(tribromomethyl)benzenesulfonic acid, 2,6-bis(triiodomethyl)benzenesulfonic acid, 3,5-bis(trifluoromethyl) benzenesulfonic acid, 3,5-bis(trichloromethyl)benzenesulfonic acid, 3,5-bis(tribromomethyl)benzenesulfonic acid and 3,5-bis(triiodomethyl)benzenesulfonic acid; aralkylsulfonic acids such as benzylsulfonic acid, phenethylsulfonic acid, phenylpropylsulfonic acid, phenylbutylsulfonic acid, phenylpentylsulfonic acid, phenylhexylsulfonic acid, phenylheptylsulfonic acid, phenyloctylsulfonic acid and phenylnonylsulfonic acid; halogenated aralkylsulfonic acids such as 4-fluorophenylmethyl sulfonic acid, 4-chlorophenylmethylsulfonic acid, 4-bromophenylmethylsulfonic acid, 4-iodophenylmethylsulfonic acid, tetrafluorophenylmethylsulfonic acid, tetrachlorophenylmethylsulfonic acid, tetrabromophenylmethylsulfonic acid, tetraiodophenylmethylsulfonic acid, 4-fluorophenylethylsulfonic acid, 4-chlorophenylethylsulfonic acid, 4-bromophenylethylsulfonic acid, 4-iodophenylethylsulfonic acid, 4-fluorophenylpropylsulfonic acid, 4-chlorophenylpropylsulfonic acid, 4-bromophenylpropylsulfonic acid, 4-iodophenylpropylsulfonic acid, 4-fluorophenylbutylsulfonic acid, 4-chlorophenylbutylsulfonic acid, 4-bromophenylbutylsulfonic acid and 4-iodophenylbutylsulfonic acid; alicyclicsulfonic acids such as camphorsulfonic acid; and salts thereof (e.g. lithium salt, sodium salt, potassium salt, rubidium salt, silver salt, cesium salt, etc.).

The preferable specific examples of inorganic strong acid represented by the general formula [7] or a salt thereof, include, for example, tetrafluoroborate, tetrafluoroaluminate, tetrafluoroferrate, tetrafluorogallate, hexafluorophosphate, hexafluoroarsenate, hexafluoroantimonate, hexafluorosilicate, hexafluoronickelate, hexafluorotitanate, hexafluorozirconate, and salts thereof (e.g. silver salt, potassium salt, sodium salt, lithium salt, etc.).

The more preferable specific examples of the triarylsulfonium salt represented by the general formula [4] include, for example, one (halogen salt) represented by the general formula [8]:

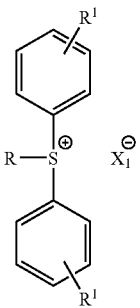

[8]

(wherein R, $R^1$ and $X_1$ are the same as mentioned above), one (sulfonic acid salt) represented by the general formula [9]:

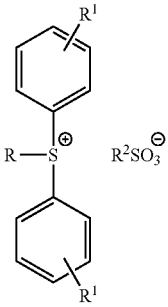

[9]

(wherein R, $R^1$ and $R^2$ are the same as mentioned above), and one (inorganic strong acid salt) represented by the general formula [10]:

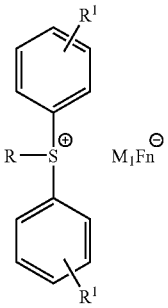

[10]

(wherein R, $R^1$, $M_1$ and n are the same as mentioned above).

The preferable specific examples of the sulfonium salt (halogen salt) represented by the general formula [8] include, for example, 4-methylphenyldiphenylsulfonium bromide, 3-methylphenyldiphenylsulfonium bromide, 2-methylphenyldiphenylsulfonium bromide, 4-tert-butylphenyldiphenylsulfonium bromide, 4-cyclohexylphenyldiphenylsulfonium bromide, 4-methoxyphenyldiphenylsulfonium bromide, 3-methoxyphenyldiphenylsulfonium bromide, 4-n-butoxyphenyldiphenylsulfonium bromide, 2-n-butoxyphenyldiphenylsulfonium bromide, 4-tert-butoxyphenyldiphenylsulfonium bromide, 4-tert-butoxyphenyldiphenylsulfonium bromide, 4-methylthiophenyldiphenylsulfonium bromide, 2,4,6-trimethylphenyldiphenylsulfonium bromide, 3,5-dimethyl-4-methoxyphenyldiphenylsulfonium bromide, 4-fluorophenyldiphenylsulfonium bromide, 4-chlorophenyldiphenylsulfonium bromide, 4-trifluoromethylphenyldiphenylsulfonium bromide, 1-naphthyldiphenylsulfonium bromide, bis(4-methylphenyl)phenylsulfonium bromide, bis(4-methoxyphenyl)phenylsulfonium bromide, bis(4-tert-butylphenyl)phenylsulfonium bromide, bis(4-trifluoromethylphenyl)phenylsulfonium bromide, bis(4-fluorophenyl)phenylsulfonium bromide, bis(4-chlorophenyl)phenylsulfonium bromide and bis(4-hydroxyphenyl)phenylsulfonium bromide.

The preferable specific examples of the sulfonium salt (halogen salt) represented by the general formula [9] include, for example, 4-methylphenyldiphenylsulfonium trifluoromethanesulfonate, 4-methylphenyldiphenylsulfonium nonafluorobutanesulfonate, 4-methylphenyldiphenylsulfonium perfluorohexanesulfonate, 4-methylphenyldiphenylsulfonium perfluorooctanesulfonate, 4-methylphenyldiphenylsulfonium p-toluenesulfonate, 4-methylphenyldiphenylsulfonium pentafluorobenzenesulfonate, 4-methylphenyldiphenylsulfonium p-trifluoromethylbenzenesulfonate, 3-methylphenyldiphenylsulfonium trifluoromethanesulfonate, 3-methylphenyldiphenylsulfonium nonafluorobutanesulfonate, 3-methylphenyldiphenylsulfonium perfluorohexanesulfonate, 3-methylphenyldiphenylsulfonium perfluorooctanesulfonate, 3-methylphenyldiphenylsulfonium p-toluenesulfonate, 3-methylphenyldiphenylsulfonium pentafluorobenzenesulfonate, 3-methylphenyldiphenylsulfonium p-trifluoromethylbenzenesulfonate, 2-methylphenyldiphenylsulfonium trifluoromethanesulfonate, 2-methylphenyldiphenylsulfonium nonafluorobutanesulfonate, 2-methylphenyldiphenylsulfonium perfluorohexanesulfonate, 2-methylphenyldiphenylsulfonium perfluorooctanesulfonate, 2-methylphenyldiphenylsulfonium p-toluenesulfonate, 2-methylphenyldiphenylsulfonium pentafluorobenzenesulfonate, 2-methylphenyldiphenylsulfonium p-trifluoromethylbenzenesulfonate, 4-tert-butylphenyldiphenylsulfonium trifluoromethanesulfonate, 4-tert-butylphenyldiphenylsulfonium nonafluorobutanesulfonate, 4-tert-butylphenyldiphenylsulfonium perfluorohexanesulfonate, 4-tert-butylphenyldiphenylsulfonium perfluorooctanesulfonate, 4-tert-butylphenyldiphenylsulfonium p-toluenesulfonate, 4-tert-butylphenyldiphenylsulfonium pentafluorobenzenesulfonate, 4-tert-butylphenyldiphenylsulfonium p-trifluoromethylbenzenesulfonate, 4-cyclohexylphenyldiphenylsulfonium trifluoromethanesulfonate, 4-cyclohexylphenyldiphenylsulfonium nonafluorobutanesulfonate, 4-cyclohexylphenyldiphenylsulfonium perfluorohexanesulfonate, 4-cyclohexylphenyldiphenylsulfonium perfluorooctanesulfonate, 4-cyclohexylphenyldiphenylsulfonium p-toluenesulfonate, 4-cyclohexylphenyldiphenylsulfonium pentafluorobenzenesulfonate, 4-cyclohexylphenyldiphenylsulfonium p-trifluoromethylbenzenesulfonate, 4-methoxyphenyldiphenylsulfonium trifluoromethanesulfonate, 4-methoxyphenyldiphenylsulfonium nonafluorobutanesulfonate, 4-methoxyphenyldiphenylsulfonium perfluorohexanesulfonate, 4-methoxyphenyldiphenylsulfonium perfluorooctanesulfonate, 4-methoxyphenyldiphenylsulfonium p-toluenesulfonate, 4-methoxyphenyldiphenylsulfonium pentafluorobenzenesulfonate, 4-methoxyphenyldiphenylsulfonium p-trifluoromethylbenzenesulfonate, 3-methoxyphenyldiphenylsulfonium trifluoromethanesulfonate, 3-methoxyphenyldiphenylsulfonium nonafluorobutanesulfonate, 3-methoxyphenyldiphenylsulfonium perfluorohexanesulfonate, 3-methoxyphenyldiphenylsulfonium perfluorooctanesulfonate, 3-methoxyphenyldiphenylsulfonium p-toluenesulfonate, 3-methoxyphenyldiphenylsulfonium pentafluorobenzenesulfonate, 3-methoxyphenyldiphenylsulfonium p-trifluoromethylbenzenesulfonate, 4-n-butoxyphenyldiphenylsulfonium trifluoromethanesulfonate, 4-n-butoxyphenyldiphenylsulfonium nonafluorobutanesulfonate, 4-n-butoxyphenyldiphenylsulfonium perfluorohexanesulfonate, 4-n-butoxyphenyldiphenylsulfonium perfluorooctanesulfonate, 4-n-butoxyphenyldiphenylsulfonium p-toluenesulfonate, 4-n-butoxyphenyldiphenylsulfonium pentafluorobenzenesulfonate, 4-n-butoxyphenyldiphenylsulfonium p-trifluoromethylbenzenesulfonate, 2-n-butoxyphenyldiphenylsulfonium trifluoromethanesulfonate, 2-n-butoxyphenyldiphenylsulfonium nonafluorobutanesulfonate, 2-n-butoxuphenyldiphenylsulfonium perfluorohexanesulfonate, 2-n-butoxyphenyldiphenylsulfonium perfluorooctanesulfonate, 2-n-butoxyphenyldiphenylsulfonium p-toluenesulfonate, 2-n-butoxyphenyldiphenylsulfonium pentafluorobenzenesulfonate, 2-n-butoxyphenyldiphenylsulfonium p-trifluoromethylbenzenesulfonate, 4-tert-butoxyphenyldiphenylsulfonium trifluoromethanesulfonate, 4-tert-butoxyphenyldiphenylsulfonium nonafluorobutanesulfonate, 4-tert-butoxyphenyldiphenylsulfonium perfluorohexanesulfonate, 4-tert-butoxyphenyldiphenylsulfonium perfluorooctanesulfonate, 4-tert-butoxyphenyldiphenylsulfonium p-toluenesulfonate, 4-tert-butoxyphenyldiphenylsulfonium pentafluorobenzenesulfonate, 4-tert-butoxyphenyldiphenylsulfonium p-trifluoromethylbenzenesulfonate, 4-tert-butoxyphenyldiphenylsulfonium trifluoromethanesulfonate, 4-tert-butoxyphenyldiphenylsulfonium nonafluorobutanesulfonate, 4-tert-butoxyphenyldiphenylsulfonium perfluorooctanesulfonate, 4-tert-butoxyphenyldiphenylsulfonium pentafluorobenzenesulfonate, 4-tert-butoxyphenyldiphenylsulfonium p-trifluoromethylbenzenesulfonate, 4-methylthiophenyldiphenylsulfonium trifluoromethanesulfonate, 4-methylthiophenyldiphenylsulfonium nonafluorobutanesulfonate, 4-methylthiophenyldiphenylsulfonium perfluorohexanesulfonate, 4-methylthiophenyldiphenylsulfonium perfluorooctanesulfonate, 4-methylphenyldiphenylsulfonium p-toluenesulfonate, 4-methylthiophenyldiphenylsulfonium pentafluorobenzenesulfonate, 4-methylthiophenyldiphenylsulfonium p-trifluoromethylbenzenesulfonate, 2,4,6-trimethylphenyldiphenylsulfonium trifluoromethanesulfonate, 2,4,6-trimethylphenyldiphenylsulfonium nonafluorobutanesulfonate, 2,4,6-trimethylphenyldiphenylsulfonium perfluorohexanesulfonate, 2,4,6-trimethylphenyldiphenylsulfonium perfluorooctanesulfonate, 2,4,6-trimethylphenyldiphenylsulfonium p-toluenesulfonate, 2,4,6-trimethylphenyldiphenylsulfonium pentafluorobenzenesulfonate, 2,4,6-trimethylphenyldiphenylsulfonium p-trifluoromethylbenzenesulfonate, 3,5-dimethyl-4-methoxyphenyldiphenylsulfonium trifluoromethanesulfonate, 3,5-dimethyl-4-methoxyphenyldiphenylsulfonium nonafluorobutanesulfonate, 3,5-dimethyl-4-methoxyphenyldiphenylsulfonium perfluorohexanesulfonate, 3,5-dimethyl-4-methoxyphenyldiphenylsulfonium perfluorooctanesulfonate, 3,5-dimethyl-4-methoxyphenyldiphenylsulfonium p-toluenesulfonate, 3,5-dimethyl-4-methoxyphenyldiphenylsulfonium pentafluorobenzenesulfonate, 3,5-dimethyl-4-methoxyphenyldiphenylsulfonium p-trifluoromethylbenzenesulfonate, 4-fluorophenyldiphenylsulfonium trifluoromethanesulfonate, 4-fluorophenyldiphenylsulfonium nonafluorobutanesulfonate, 4-fluorophenyldiphenylsulfonium perfluorohexanesulfonate, 4-fluorophenyldiphenylsulfonium perfluorooctanesulfonate, 4-fluorophenyldiphenylsulfonium p-toluenesulfonate, 4-fluorophenyldiphenylsulfonium pentafluorobenzenesulfonate, 4-fluorophenyldiphenylsulfonium p-trifluoromethylbenzenesulfonate, 4-chlorophenyldiphenylsulfonium trifluoromethanesulfonate, 4-chlorophenyldiphenylsulfonium nonafluorobutanesulfonate, 4-chlorophenyldiphenylsulfonium perfluorohexanesulfonate, 4-chlorophenyldiphenylsulfonium perfluorooctanesulfonate, 4-chlorophenyldiphenylsulfonium p-toluenesulfonate, 4-chlorophenyldiphenylsulfonium pentafluorobenzenesulfonate, 4-chlorophenyldiphenylsulfonium p-trifluoromethylbenzenesulfonate, 4-trifluoromethylphenyldiphenylsulfonium trifluoromethanesulfonate, 4-trifluoromethylphenyldiphenylsulfonium nonafluorobutanesulfonate, 4-trifluoromethylphenyldiphenylsulfonium perfluorohexanesulfonate, 4-trifluoromethylphenyldiphenylsulfonium perfluorooctanesulfonate, 4-trifluoromethylphenyldiphenylsulfonium p-toluenesulfonate, 4-trifluoromethylphenyldiphenylsulfonium pentafluorobenzenesulfonate, 4-trifluoromethylphenyldiphenylsulfonium p-trifluoromethylbenzenesulfonate, 1-naphthyldiphenylsulfonium trifluoromethanesulfonate, 1-naphtyldiphenylsulfonium nonafluorobutanesulfonate, 1-naphtyldiphenylsulfonium perfluorohexanesulfonate, 1-naphtyldiphenylsulfonium perfluorooctanesulfonate, 1-naphtyldiphenylsulfonium p-toluenesulfonate, 1-naphthyldiphenylsulfonium pentafluorobenzenesulfonate, 1-naphthyldiphenylsulfonium p-trifluoromethylbenzenesulfonate, bis(4-methylphenyl)phenylsulfonium trifluoromethanesulfonate, bis(4-methylphenyl)phenylsulfonium nonafluorobutanesulfonate, bis(4-methylphenyl)phenylsulfonium perfluorohexanesulfonate, bis(4-methylphenyl)phenylsulfonium perfluorooctanesulfonate, bis(4-methylphenyl)phenylsulfonium p-toluenesulfonate, bis(4-methylphenyl)phenylsulfonium pentafluorobenzenesulfonate, bis(4-methylphenyl)phenylsulfonium p-trifluoromethylbenzenesulfonate, bis(4-methoxyphenyl)phenylsulfonium trifluoromethanesulfonate, bis(4-methoxyphenyl)phenylsulfonium nonafluorobutanesulfonate, bis(4-methoxyphenyl)phenylsulfonium perfluorohexanesulfonate, bis(4-methoxyphenyl)phenylsulfonium perfluorooctanesulfonate, bis(4-methoxyphenyl)phenylsulfonium p-toluenesulfonate, bis(4-methoxyphenyl)phenylsulfonium pentafluorobenzenesulfonate, bis(4-methoxyphenyl)phenylsulfonium p-trifluoromethylbenzenesulfonate, bis(4-tert-butylphenyl)phenylsulfonium trifluoromethanesulfonate, bis(4-tert-butylphenyl)phenylsulfonium nonafluorobutanesulfonate, bis(4-tert-butylphenyl)phenylsulfonium perfluorohexanesulfonate, bis(4-tert-butylphenyl)phenylsulfonium perfluorooctanesulfonate, bis(4-tert-butylphenyl)phenylsulfonium p-toluenesulfonate, bis(4-tert-butylphenyl)phenylsulfonium pentafluorobenzenesulfonate, bis(4-tert-butylphenyl)phenylsulfonium p-trifluoromethylbenzenesulfonate, bis(4-trifluoromethylphenyl)phenylsulfonium trifluoromethanesulfonate, bis(4-trifluoromethylphenyl)phenylsulfonium nonafluorobutanesulfonate, bis(4-trifluoromethylphenyl)phenylsulfonium perfluorohexanesulfonate, bis(4-trifluoromethylphenyl)phenylsulfonium perfluorooctanesulfonate, bis(4-trifluoromethylphenyl)phenylsulfonium p-toluenesulfonate, bis(4-trifluoromethylphenyl)phenylsulfonium pentafluorobenzenesulfonate, bis(4-trifluoromethylphenyl)phenylsulfonium p-trifluoromethylbenzenesulfonate, bis(4-fluorophenyl)phenylsulfonium trifluoromethanesulfonate, bis(4-fluorophenyl)phenylsulfonium nonafluorobutanesulfonate, bis(4-fluorophenyl)phenylsulfonium perfluorohexanesulfonate, bis(4-fluorophenyl)phenylsulfonium perfluorooctanesulfonate, bis(4-fluorophenyl)phenylsulfonium p-toluenesulfonate, bis(4-fluorophenyl)phenylsulfonium pentafluorobenzenesulfonate, bis(4-fluorophenyl)phenylsulfonium p-trifluoromethylbenzenesulfonate, bis(4-chlorophenyl)phenylsulfonium trifluoromethanesulfonate, bis(4-chlorophenyl)phenylsulfonium nonafluorobutanesulfonate, bis(4-chlorophenyl)phenylsulfonium perfluorohexanesulfonate, bis(4-chlorophenyl)phenylsulfonium perfluorooctanesulfonate, bis(4-chlorophenyl)phenylsulfonium p-toluenesulfonate, bis(4-chlorophenyl)phenylsulfonium pentafluorobenzenesulfonate, bis(4-chlorophenyl)phenylsulfonium p-trifluoromethylbenzenesulfonate, bis(4-hydroxyphenyl)phenylsulfonium trifluoromethanesulfonate, bis(4-hydroxyphenyl)phenylsulfonium nonafluorobutanesulfonate, bis(4-hydroxyphenyl)phenylsulfonium perfluorohexanesulfonate, bis(4-hydroxyphenyl)phenylsulfonium perfluorooctanefonate, bis(4-hydroxyphenyl)phenylsulfonium p-toluenesulfonate, bis(4-hydroxyphenyl)phenylsulfonium pentafluorobenzenesulfonate and bis(4-hydroxyphenyl)phenylsulfonium p-trifluoromethylbenzenesulfonate.

The preferable specific examples of the sulfonium salt (inorganic strong acid salt) represented by the general formula [10] include, for example, 4-methylphenyldiphenylsulfonium perchlorate, 4-methylphenyldiphenylsulfonium tetrafluoroborate, 4-methylphenyldiphenylsulfonium hexafluorophosphate, 4-methylphenyldiphenylsulfonium hexafluoroarsenate, 4-methylphenyldiphenylsulfonium hexafluoroantimonate, 4-methylphenyldiphenylsulfonium tetraphenylborate, 4-methylphenyldiphenylsulfonium tetrakis{3,5-bis(trifluoromethyl)phenyl}borate, 4-methylphenyldiphenylsulfonium tetrakis(pentafluorophenyl)borate, 4-methylphenyldiphenylsulfonium tetraphenylgallate, 4-methylphenyldiphenylsulfonium tetrakis(pentafluorophenyl)gallate, 3-methylphenyldiphenylsulfonium perchlorate, 3-methylphenyldiphenylsulfonium tetrafluoroborate, 3-methylphenyldiphenylsulfonium hexafluorophosphate, 3-methylphenyldiphenylsulfonium hexafluoroarsenate, 3-methylphenyldiphenylsulfonium hexafluoroantimonate, 3-methylphenyldiphenylsulfonium tetraphenylborate, 3-methylphenyldiphenylsulfonium tetrakis{3,5-bis(trifluoromethyl)phenyl}borate, 3-methylphenyldiphenylsulfonium tetrakis(pentafluorophenyl)borate, 3-methylphenyldiphenylsulfonium tetraphenylgallate, 3-methylphenyldiphenylsulfonium tetrakis(pentafluorophenyl)gallate, 2-methylphenyldiphenylsulfonium perchlorate, 2-methylphenyldiphenylsulfonium tetrafluoroborate, 2-methylphenyldiphenylsulfonium hexafluorophosphate, 2-methylphenyldiphenylsulfonium hexafluoroarsenate, 2-methylphenyldiphenylsulfonium hexafluoroantimonate, 2-methylphenyldiphenylsulfonium tetraphenylborate, 2-methylphenyldiphenylsulfonium tetrakis{3,5-bis(trifluoromethyl)phenyl}borate, 2-methylphenyldiphenylsulfonium tetrakis(pentafluorophenyl)borate, 2-methylphenyldiphenylsulfonium tetraphenylgallate, 2-methylphenyldiphenylsulfonium tetrakis(pentafluorophenyl)gallate, 4-tert-butylphenyldiphenylsulfonium perchlorate, 4-tert-butylphenyldiphenylsulfonium tetrafluoroborate, 4-tert-butylphenyldiphenylsulfonium hexafluorophosphate, 4-tert-butylphenyldiphenylsulfonium hexafluoroarsenate, 4-tert-butylphenyldiphenylsulfonium hexafluoroantimonate, 4-tert-butylphenyldiphenylsulfonium tetraphenylborate, 4-tert-butylphenyldiphenylsulfonium tetrakis{3,5-bis(trifluoromethyl)phenyl}borate, 4-tert-butylphenyldiphenylsulfonium tetrakis(pentafluorophenyl)borate, 4-tert-butylphenyldiphenylsulfonium tetraphenylgallate, 4-tert-butylphenyldiphenylsulfonium tetrakis(pentafluorophenyl)gallate, 4-cyclohexylphenyldiphenylsulfonium perchlorate, 4-cyclohexylphenyldiphenylsulfonium tetrafluoroborate, 4-cyclohexylphenyldiphenylsulfonium hexafluorophosphate, 4-cyclohexylphenyldiphenylsulfonium hexafluoroarsenate, 4-cyclohexylphenyldiphenylsulfonium hexafluoroantimonate, 4-cyclohexylphenyldiphenylsulfonium tetraphenylborate, 4-cyclohexylphenyldiphenylsulfonium tetrakis{3,5-bis(trifluoromethyl)phenyl}borate, 4-cyclohexylphenyldiphenylsulfonium tetrakis(pentafluorophenyl)borate, 4-cyclohexylphenyldiphenylsulfonium tetraphenylgallate, 4-cyclohexylphenyldiphenylsulfonium tetrakis(pentafluorophenyl)gallate, 4-methoxyphenyldiphenylsulfonium perchlorate, 4-methoxyphenyldiphenylsulfonium tetrafluoroborate, 4-methoxyphenyldiphenylsulfonium hexafluorophosphate, 4-methoxyphenyldiphenylsulfonium hexafluoroarsenate, 4-methoxyphenyldiphenylsulfonium hexafluoroantimonate, 4-methoxyphenyldiphenylsulfonium tetraphenylborate, 4-methoxyphenyldiphenylsulfonium tetrakis{3,5-bis(trifluoromethyl)phenyl}borate, 4-methoxyphenyldiphenylsulfonium tetrakis(pentafluorophenyl)borate, 4-methoxyphenyldiphenylsulfonium tetraphenylgallate, 4-methoxyphenyldiphenylsulfonium tetrakis(pentafluorophenyl)gallate, 3-methoxyphenyldiphenylsulfonium perchlorate, 3-methoxyphenyldiphenylsulfonium tetrafluoroborate, 3-methoxyphenyldiphenylsulfonium hexafluorophosphate, 3-methoxyphenyldiphenylsulfonium hexafluoroarsenate, 3-methoxyphenzyldiphenylsulfonium hexafluoroantimonate, 3-methoxyphenyldiphenylsulfonium tetraphenylborate, 3-methoxyphenyldiphenylsulfonium tetrakis{3,5-bis(trifluoromethyl)phenyl}borate, 3-methoxyphenyldiphenylsulfonium tetrakis(pentafluorophenyl)borate, 3-methoxyphenyldiphenylsulfonium tetraphenylgallate, 3-methoxyphenyldiphenylsulfonium tetrakis(pentafluorophenyl)gallate, 4-n-butoxyphenyldiphenylsulfonium perchlorate, 4-n-butoxyphenyldiphenylsulfonium tetrafluoroborate, 4-n-butoxyphenyldiphenylsulfonium hexafluorophosphate, 4-n-butoxyphenyldiphenylsulfonium hexafluoroarsenate, 4-n-butoxyphenyldiphenylsulfonium hexafluoroantimonate, 4-n-butoxyphenyldiphenylsulfonium tetraphenylborate, 4-n-butoxyphenyldiphenylsulfonium tetrakis{3,5-bis(trifluoromethyl)phenyl}borate, 4-n-butoxyphenyldiphenylsulfonium tetrakis(pentafluorophenyl)borate, 4-n-butoxyphenyldiphenylsulfonium tetraphenylgallate, 4-n-butoxyphenyldiphenylsulfonium tetrakis(pentafluorophenyl)gallate, 2-n-butoxyphenyldiphenylsulfonium perchlorate, 2-n-butoxyphenyldiphenylsulfonium tetrafluoroborate, 2-n-butoxyphenyldiphenylsulfonium hexafluorophosphate, 2-n-butoxyphenyldiphenylsulfonium hexafluoroarsenate, 2-n-butoxyphenyldiphenylsulfonium hexafluoroantimonate, 2-n-butoxyphenyldiphenylsulfonium tetraphenylborate, 2-n-butoxyphenyldiphenylsulfonium tetrakis{3,5-bis(trifluoromethyl)phenyl}borate, 2-n-butoxyphenyldiphenylsulfonium tetrakis(pentafluorophenyl)borate, 2-n-butoxyphenyldiphenylsulfonium tetraphenylgallate, 2-n-butoxyphenyldiphenylsulfonium tetrakis(pentafluorophenyl)gallate, 4-tert-butoxyphenyldiphenylsulfonium perchlorate, 4-tert-butoxyphenyldiphenylsulfonium tetrafluoroborate, 4-tert-butoxyphenyldiphenylsulfonium hexafluorophosphate, 4-tert-butoxyphenyldiphenylsulfonium hexafluoroarsenate, 4-tert-butoxyphenyldiphenylsulfonium hexafluoroantimonate, 4-tert-butoxyphenyldiphenylsulfonium tetraphenylborate, 4-tert-butoxyphenyldiphenylsulfonium tetrakis{3,5-bis(trifluoromethyl)phenyl}borate, 4-tert-butoxyphenyldiphenylsulfonium tetrakis(pentafluorophenyl)borate, 4-tert-butoxyphenyldiphenylsulfonium tetraphenylgallate, 4-tert-butoxyphenyldiphenylsulfonium tetrakis(pentafluorophenyl)gallate, 2,4,6-trimethylphenyldiphenylsulfonium perchlorate, 2,4,6-trimethylphenyldiphenylsulfonium tetrafluoroborate, 2,4,6-trimethylphenyldiphenylsulfonium hexafluorophosphate, 2,4,6-trimethylphenyldiphenylsulfonium hexafluoroarsenate, 2,4,6-trimethylphenyldiphenylsulfonium hexafluoroantimonate, 2,4,6-trimethylphenyldiphenylsulfonium tetraphenylborate, 2,4,6-trimethylphenyldiphenylsulfonium tetrakis{3,5-bis(trifluoromethyl)phenyl}borate, 2,4,6-trimethylphenyldiphenylsulfonium tetrakis(pentafluorophenyl)borate, 2,4,6-trimethylphenyldiphenylsulfonium tetraphenylgallate, 2,4,6-trimethylphenyldiphenylsulfonium tetrakis(pentafluorophenyl)gallate, 4-methylthiophenyldiphenylsulfonium perchlorate, 4-methylthiophenyldiphenyl sulfonium tetrafluoroborate, 4-methylthiophenyldiphenylsulfonium hexafluorophosphate, 4-methylthiophenyldiphenylsulfonium hexafluoroarsenate, 4-methylthiophenyldiphenylsulfonium hexafluoroantimonate, 4-methylthiophenyldiphenylsulfonium tetraphenylborate, 4-methylthiophenyldiphenylsulfonium tetrakis{3,5-bis(trifluoromethyl)phenyl}borate, 4-methylthiophenyldiphenylsulfonium tetrakis(pentafluorophenyl)borate, 4-methythiophenyldiphenylsulfonium tetraphenylgallate, 4-methylthiophenyldiphenylsulfonium tetrakis(pentafluorophenyl)gallate, 3,5-dimethyl-4-methoxyphenyldiphenylsulfonium perchlorate, 3,5-dimethyl-4-methoxyphenyldiphenylsulfonium tetrafluoroborate, 3,5-dimethyl-4-methoxyphenyldiphenylsulfonium hexafluorophosphate, 3,5-dimethyl-4-methoxyphenyldiphenylsulfonium hexafluoroarsenate, 3,5-dimethyl-4-methoxyphenyldiphenylsulfonium hexafluoroantimonate, 3,5-dimethyl-4-methoxyphenyldiphenylsulfonium tetraphenylborate, 3,5-dimethyl-4-methoxyphenyldiphenylsulfonium tetrakis{3,5-bis(trifluoromethyl)phenyl}borate, 3,5-dimethyl-4-methoxyphenyldiphenylsulfonium tetrakis(pentafluorophenyl)borate, 3,5-dimethyl-4-methoxyphenyldiphenylsulfonium tetraphenylgallate, 3,5-dimethyl-4-methoxyphenyldiphenylsulfonium tetrakis(pentafluorophenyl)gallate, 4-fluorophenyldiphenylsulfonium perchlorate, 4-fluorophenyldiphenylsulfonium tetrafluoroborate, 4-fluorophenyldiphenylsulfonium hexafluorophosphate, 4-fluorophenyldiphenylsulfonium hexafluoroarsenate, 4-fluorophenyldiphenylsulfonium hexafluoroantimonate, 4-fluorophenyldiphenylsulfonium tetraphenylborate, 4-fluorophenyldiphenylsulfonium tetrakis{3,5-bis(trifluoromethyl)phenyl}borate, 4-fluorophenyldiphenylsulfonium tetrakis(pentafluorophenyl)borate, 4-fluorophenyldiphenylsulfonium tetraphenylgallate, 4-fluorophenyldiphenylsulfonium tetrakis(pentafluorophenyl)gallate, 4-chlorophenyldiphenylsulfonium perchlorate, 4-chlorophenyldiphenylsulfonium tetrafluoroborate, 4-chlorophenyldiphenylsulfonium hexafluorophosphate, 4-chlorophenyldiphenylsulfonium hexafluoroarsenate, 4-chlorophenyldiphenylsulfonium hexafluoroantimonate, 4-chlorophenyldiphenylsulfonium tetraphenylborate, 4-chlorophenyldiphenylsulfonium tetrakis{3,5-bis(trifluoromethyl)phenyl}borate, 4-chlorophenyldiphenylsulfonium tetrakis(pentafluorophenyl)borate, 4-chlorophenyldiphenylsulfonium tetraphenylgallate, 4-chlorophenyldiphenylsulfonium tetrakis(pentafluorophenyl)gallate, 4-trifluoromethylphenyldiphenylsulfonium perchlorate, 4-trifluoromethylphenyldiphenylsulfonium tetrafluoroborate, 4-trifluoromethylphenyldiphenylsulfonium hexafluorophosphate, 4-trifluoromethylphenyldiphenylsulfonium hexafluoroarsenate, 4-trifluoromethylphenyldiphenylsulfonium hexafluoroantimonate, 4-trifluoromethylphenyldiphenylsulfonium tetraphenylborate, 4-trifluoromethylphenyldiphenylsulfonium tetrakis{3,5-bis(trifluoromethyl)phenyl}borate, 4-trifluoromethylphenyldiphenylsulfonium tetrakis(pentafluorophenyl)borate, 4-trifluoromethylphenyldiphenylsulfonium tetraphenylgallate, 4-trifluoromethylphenyldiphenylsulfonium tetrakis(pentafluorophenyl)gallate, bis(4-methylphenyl)phenylsulfonium perchlorate, bis(4-methylphenyl)phenylsulfonium tetrafluoroborate, bis(4-methylphenyl)phenylsulfonium hexafluorophosphate, bis(4-methylphenyl)phenylsulfonium hexafluoroarsenate, bis(4-methylphenyl)phenylsulfonium hexafluoroantimonate, bis(4-methylphenyl)phenylsulfonium tetraphenylborate, bis(4-methylphenyl)phenylsulfonium tetrakis{3,5-bis(trifluoromethyl)phenyl}borate, bis(4-methylphenyl)phenylsulfonium tetrakis(pentafluorophenyl)borate, bis(4-methylphenyl)phenylsulfonium tetraphenylgallate, bis(4-methylphenyl)phenylsulfonium tetrakis(pentafluorophenyl)gallate, bis(4-methoxyphenyl)phenylsulfonium perchlorate, bis(4-methoxyphenyl)phenylsulfonium tetrafluoroborate, bis(4-methoxyphenyl)phenylsulfonium hexafluorophosphate, bis(4-methoxyphenyl)phenylsulfonium hexafluoroarsenate, bis(4-methoxyphenyl)phenylsulfonium hexafluoroantimonate, bis(4-methoxyphenyl)phenylsulfonium tetraphenylborate, bis(4-methoxyphenyl)phenylsulfonium tetrakis{3,5-bis(trifluoromethyl)phenyl}borate, bis(4-methoxyphenyl)phenylsulfonium tetrakis(pentafluorophenyl)borate, bis(4-methoxyphenyl)phenylsulfonium tetraphenylgallate, bis(4-methoxyphenyl)phenylsulfonium tetrakis(pentafluorophenyl)gallate, bis(4-tert-butylphenyl)phenylsulfonium perchlorate, bis(4-tert-butylphenyl)phenylsulfonium tetrafluoroborate, bis(4-tert-butylphenyl)phenylsulfonium hexafluorophosphate, bis(4-tert-butylphenyl)phenylsulfonium hexafluoroarsenate, bis(4-tert-butylphenyl)phenylsulfonium hexafluoroantimonate, bis(4-tert-butylphenyl)phenylsulfonium tetraphenylborate, bis(4-tert-butylphenyl)phenylsulfonium tetrakis{3,5-bis(trifluoromethyl)phenyl}borate, bis(4-tert-butylphenyl)phenylsulfonium tetrakis(pentafluorophenyl)borate, bis(4-tert-butylphenyl)phenylsulfonium tetraphenylgallate, bis(4-tert-butylphenyl)phenylsulfonium tetrakis(pentafluorophenyl)gallate, bis(4-trifluoromethylphenyl)phenylsulfonium perchlorate, bis(4-trifluoromethylphenyl)phenylsulfonium tetrafluoroborate, bis(4-trifluoromethylphenyl)phenylsulfonium hexafluorophosphate, bis(4-trifluoromethylphenyl)phenylsulfonium hexafluoroarsenate, bis(4-trifluoromethylphenyl)phenylsulfonium hexafluoroantimonate, bis(4-trifluoromethylphenyl)phenylsulfonium tetraphenylborate, bis(4-trifluoromethylphenyl)phenylsulfonium tetrakis{3,5-bis(trifluoromethyl)phenyl}borate, bis(4-trifluoromethylphenyl)phenylsulfonium tetrakis(pentafluorophenyl)borate, bis(4-trifluoromethylphenyl)phenylsulfonium tetraphenylgallate, bis(4-trifluoromethylphenyl)phenylsulfonium tetrakis(pentafluorophenyl)gallate, 1-naphthyldiphenylsulfonium perchlorate, 1-naphthyldiphenylsulfonium tetrafluoroborate, 1-naphthyldiphenylsulfonium hexafluorophosphate, 1-naphthyldiphenylsulfonium hexafluoroarsenate, 1-naphthyldiphenylsulfonium hexafluoroantimonate, 1-naphthyldiphenylsulfonium tetraphenylborate, 1-naphthyldiphenylsulfonium tetrakis{3,5-bis(trifluoromethyl)phenyl}borate, 1-naphthyldiphenylsulfonium tetrakis(pentafluorophenyl)borate, 1-naphthyldiphenylsulfonium tetraphenylgallate, 1-naphthyldiphenylsulfonium tetrakis(pentafluorophenyl)gallate, bis(4-fluorophenyl)phenylsulfonium perchlorate, bis(4-fluorophenyl)phenylsulfonium tetrafluoroborate, bis(4-fluorophenyl)phenylsulfonium hexafluorophosphate, bis(4-fluorophenyl)phenylsulfonium hexafluoroarsenate, bis(4-fluorophenyl)phenylsulfonium hexafluoroantimonate, bis(4-fluorophenyl)phenylsulfonium tetraphenylborate, bis(4-fluorophenyl)phenylsulfonium tetrakis{3,5-bis(trifluoromethyl)phenyl}borate, bis(4-fluorophenyl)phenylsulfonium tetrakis(pentafluorophenyl)borate, bis(4-fluorophenyl)phenylsulfonium tetraphenylgallate, bis(4-fluorophenyl)phenylsulfonium tetrakis(pentafluorophenyl)gallate, bis(4-chlorophenyl)phenylsulfonium perchlorate, bis(4-chlorophenyl)phenylsulfonium tetrafluoroborate, bis(4-chlorophenyl)phenylsulfonium hexafluorophosphate, bis(4-chlorophenyl)phenylsulfonium hexafluoroarsenate, bis(4-chlorophenyl)phenylsulfonium hexafluoroantimonate, bis(4-chlorophenyl)phenylsulfonium tetraphenylborate, bis(4-chlorophenyl)phenylsulfonium tetrakis{3,5-bis(trifluoromethyl)phenyl}borate, bis(4-chlorophenyl)phenylsulfonium tetrakis(pentafluorophenyl)borate, bis(4-chlorophenyl)phenylsulfonium tetraphenylgallate, bis(4-chlorophenyl)phenylsulfonium tetrakis(pentafluorophenyl)gallate, bis(4-hydroxyphenyl)phenylsulfonium perchlorate, bis(4-hydroxyphenyl)phenylsulfonium tetrafluoroborate, bis(4-hydroxyphenyl)phenylsulfonium hexafluorophosphate, bis(4-hydroxyphenyl)phenylsulfonium hexafluoroarsenate bis(4-hydroxyphenyl)phenylsulfonium hexafluoroantimonate, bis(4-hydroxyphenyl)phenylsulfonium tetraphenylborate, bis(4-hydroxyphenyl)phenylsulfonium tetrakis{3,5-bis(trifluoromethyl)phenyl}borate, bis(4-hydroxyphenyl)phenylsulfonium tetrakis(pentafluorophenyl)borate, bis(4-hydroxyphenyl)phenylsulfonium tetraphenylgallate and bis(4-hydroxyphenyl)phenylsulfonium tetrakis(pentafluorophenyl)gallate.

The sulfonium salt represented by the general formula [4] can be synthesized by the following method.

The diaryl sulfoxide represented by the general formula [1] is dissolved in an appropriate solvent and added with the activator with high affinity for an oxygen atom (hereinafter, abbreviated as an activator relating to the present invention) to obtain a homogenous solution. In contrast, an aryl Grignard reagent represented by the general formula [2] is prepared according to a common method, and then the above homogenous solution of the diaryl sulfoxide and the activator relating to the present invention is added thereto at −78 to 50° C., followed by reacting for under-stirring for 0.1 to 2 hours. After termination of the reaction, the obtained reaction mixture is reacted at 0 to 50° C. with the strong acid represented by the general formula [3] or a salt thereof to obtain the triarylsulfonium salt represented by the general formula [4].

The diaryl sulfoxide represented by the general formula [1] may be a commercially available product or one synthesized appropriately according to a common method (e.g. Ber., 23, 1844 (1890), J. Chem. Soc. (C), 2424 (1969), Synlett, 2003 (13), p. 2029, etc.).

The aryl Grignard reagent represented by the general formula [2] may be a commercially available product or one synthesized appropriately according to a common method.

An amount of use of the activator relating to the present invention depends on kinds of the diaryl sulfoxide represented by the general formula [1] to be used, the aryl Grignard reagent represented by the general formula [2] to be used and a solvent to be used, and the lower limit thereof is preferably in the order of 3, 4 and 4.5 equivalents and the upper limit thereof is preferably in the order of 7.5, 7 and 6 equivalents, relative to an amount of the diaryl sulfoxide, and the lower limit thereof is preferably in the order of 1.2, 1.6 and 1.8 equivalents and the upper limit thereof is preferably in the order of 3, 2.8 and 2.4 equivalents, relative to an amount of the aryl Grignard reagent.

An amount of use of the aryl Grignard reagent represented by the general formula [2] depends on kinds of the diaryl sulfoxide represented by the general formula [1] to be used and a solvent to be used, and is 1.0 to 10 equivalents, preferably 2.0 to 5.0 equivalents, relative to an amount of the diaryl sulfoxide.

The reaction solvent to be used includes ethers such as ethyl ether, isopropyl ether, tetrahydrofuran, dioxane, 1,2-dimethoxyethane, tert-buthyl methyl ether and cyclopentyl methyl ether, halogenated hydrocarbons such as methylene chloride, methylene bromide, 1,2-dichloroethane and chloroform and aromatic hydrocarbons such as benzene, toluene and xylene. These solvents may be used alone or in a suitable combination of two or more kinds thereof.

A halogen salt among triarylsulfonium salts obtained by the method of the present invention can be obtained according to an ordinary method (see, e.g. WO2002/092559, etc. Namely, the halogen salts are dissolved in alcohols such as methanol, ethanol and isopropanol, and treated with silver oxide and then various acids of 1.0 to 5.0 times by mole is added thereto. After formed silver halide is filtered off and the alcohols are evaporated off, the mixture is dissolved again in an organic solvents such as methylene chloride, 1,2-dichloroethane, ethyl acetate, butyl acetate, propylene glycol monomethyl ether acetate, methyl isobutyl ketone and methyl ethyl ketone. The obtained solution is washed with water and then concentrated under reduced pressure to obtain a triarylsulfonium salt of which the halogen atom as the counter anion is substituted with a counter anion derived from an objective acid.

In the case of reaction in two layers system, the triarylsulfonium salt is dissolved in two layer solvents of water and an organic solvent such as methylene chloride, 1,2-dichloroethane, ethyl acetate, butyl acetate, propylene glycol monomethyl ether acetate, methyl isobutyl ketone and methyl ethyl ketone, and reacted with various acids or their alkaline metal salt or their alkaline-earth metal salt of 1.0 to 5.0 times by mole. After termination of the reaction, the obtained reaction mixture is washed with water and then concentrated under reduced pressure to obtain a triarylsulfonium salt of which the halogen atom as the counter anion is substituted with a counter anion derived from an objective acid.

Post-treatment after the reaction may be conducted according to a common method in this field.

The method for producing a triarylsulfonium salt, of the present invention can efficiently produce a triarylsulfonium salt relating to the present invention in a high yield by using a larger amount of an activator relating to the present invention than that conventionally used, without having such problems accompanied with conventional method as severe reaction conditions under high temperature (e.g. reflux operation by heating, melt reaction, etc.), generation of sulfurous acid gas, drainage of a large amount of aluminum waste liquid, production of a sulfonium salt alone having the same three aromatic rings on the cation portion and formation of byproducts as impurities.

Further, a triarylsulfonium salt relating to the present invention can easily produce a triarylsulfonium salt of which the counter anion is substituted with an objective counter anion, by reacting with a compound derived from an objective anion.

Furthermore, because a triarylsulfonium salt produced by the method of the present invention contains an extremely small amount of byproducts, use of the triarylsulfonium salt as an acid generating agent can expect such effects as improvement of roughness on a profile or a sidewall of a hyperfine pattern and formation of a good rectangle pattern of reduced edge roughness.

The present invention will be explained in detail referring to the following examples, experimental examples and comparative examples, but the present invention is not limited thereto by any means.

EXAMPLE

Example 1

Synthesis of 4-methylphenyldiphenylsulfonium bromide

In a 4-methylphenyl Grignard reagent of 1.32 L (1.88 mol, 1.42 mol/L, 2.5 equiv.) prepared by a common method from 4-bromotoluene and magnesium as raw materials using tetrahydrofuran (THF) as a solvent was added a solution dissolving diphenyl sulfoxide of 151.71 g (0.75 mol, 1 equiv.) and chlorotrimethylsilane (TMSCl) of 407.25 g (3.75 mol, 5 equiv.) in THF of 0.6 L at −5° C. to room temperature, followed by reacting under stirring for 30 minutes. After termination of the reaction, the resultant reaction mixture was poured into 12% hydrobromic acid of 1.1 L and extracted two times with dichloromethane of 1.8 L. The obtained product was washed with water and then concentrated to dryness and crystallized in acetone of 1.8 L to obtain the product of 203.7 g as a white crystal (yield: 76%). Property data thereof are shown in Table 1.

Examples 2 to 16

Synthesis of Various Sulfonium Salts

The same procedure as in Example 1 was carried out except for using the predetermined aryl halides shown in Tables 1 to 3 as an aryl halide instead of 4-bromotoluene used in Example 1, to obtain objective compounds. The results are shown in Tables 1 to 3.

TABLE 1

| Exam. | aryl halide | product | Physical property data |
|---|---|---|---|
| 1 | 4-bromo-toluene | 4-methylphenyl-diphenylsulfonium bromide | yield: 76%; m.p.; 243.1-243.6° C.; $^1$H-NMR(400 MHz, CDCl$_3$) δ = 7.84-7.71(12H, m, Ph), 6.73(2H, d, J = 8.54 Hz, Ph), 2.48 (3H, s, CH$_3$); IR(KBr)(cm$^{-1}$) = 3069, 3045, 2984, 2359, 1591, 1475, 1446, 1309, 1188, 1155, 1066, 995, 808, 763, 686 |
| 2 | 3-bromo-toluene | 3-methylphenyl-diphenylsulfonium bromide | yield: 77%; m.p.: 126.7-128° C.; $^1$H-NMR(400 MHz, CDCl$_3$) δ = 7.87-7.84(4H, m, Ph), 7.82-7.72 (6H, m, Ph), 7.64-7.57 (4H, m, Ph), 2.46(3H, s, CH$_3$); IR(KBr) (cm$^{-1}$) = 3440, 3079, 3030, 1622, 1599, 1476, 1445, 1317, 1068, 995, 789, 767, 750, 684 |
| 3 | 2-bromo-toluene | 2-methylphenyl-diphenylsulfonium bromide | yield: 64%, m.p.: 228.6-228.9° C.; $^1$H-NMR(400 MHz, CDCl$_3$) δ = 7.86-7.73(10H, m, Ph), 7.68-7.65 (1H, m, Ph), 7.55-7.32 (2H, m, Ph), 7.09(1H, J = 8.30 Hz, Ph), 2.66(3H, s, CH$_3$); IR(KBr) (cm$^{-1}$) = 3476, 3404, 3077, 2993, 2338, 1591, 1476, 1446, 1278, 1178, 1159, 1072, 995, 765, 688 |
| 4 | 1-bromo-4-tert-butylbenzene | 4-tert-butylphenyldi-phenylsulfonium bromide | yield: 79%; m.p.: 232.0-233.2° C.; $^1$H-NMR(400 MHz, CDCl$_3$) δ = 7.87-7.70(14H, m, Ph), 1.35(9H, s, (CH$_3$)$_3$); IR(KBr)(cm$^{-1}$) = 3045, 2966, 1587, 1473, 1444, 1396, 1363, 1309, 1194, 1178, 1113, 1072, 995, 852, 823, 763, 688 |
| 5 | 1-bromo-4-cyclohexyl-benzene | 4-cyclohexylphenyl-diphenylsulfonium bromide | yield: 93%; m.p. 232.0-233.2° C.; $^1$H-NMR(400 MHz, CDCl$_3$) δ = 7.85-7.54 (12H, m, Ph), 7.54-7.51 (2H, m, Ph), 2.61(1H, dt, J = 6.35 Hz, J = 2.44 Hz, CR), 1.95-1.81(4H, m, CH$_2$), 1.76(1H, dddd, J − 1.47 Hz, J = 2.68 Hz, J = 8.00 Hz, J = 13.03 Hz, CH), 1.30-1.19(4H, m, CH$_2$), 1.25(1H, dddd, J = 3.14 Hz, J = 7.20 Hz, J = 8.70 Hz, J = 25.64 Hz, CH$_2$) ; IR(KBr)(cm$^{-1}$) = 3412, 2924, 2851, 2091, 1585, 1475, 1444, 1410, 1327, 1186, 1111, 1068, 1022, 997, 835, 754, 684 |
| 6 | 1-bromo-4-methoxy-benzene | 4-methoxyphenyl-diphenylsulfonium bromide | yield: 91%; m.p.: 155.0-156.3° C.; $^1$H-NMR(400 MHz, CDCl$_3$) δ = 7.89(2H, dd, J = 1.95 Hz, J = 7.08 Hz, Ph), 7.80-7.68(10H, m, Ph), 7.23(2H, dd, J = 1.95 Hz, J = 7.08 Hz, Ph), 3.92(3H, s, CH$_3$O); IR(KBr)(cm$^{-1}$) = 3481, 3393, 3080, 2841, 2575, 2019, 1587, 1495, 1475, 1444, 1415, 1311, 1269, 1178, 1116, 1070, 1016, 939, 856, 837, 798, 756, 686 |

TABLE 2

| Exam. | aryl halide | product | Physical property data |
|---|---|---|---|
| 7 | 1-bromo-3-methoxybenzene | 3-methoxyphenyl-diphenylsulfonium bromide | yield: 77%; m.p.: 88.4-89.8° C.; $^1$H-NMR(400 MHz, CDCl$_3$) δ = 7.89-7.83(4H, m, Ph), 7.80-7.67(6H, m, Ph), 7.63(1H, s, Ph), 7.59(1H, t, J = 8.18 Hz, Ph), 7.25(1H, d, J = 8.18 Hz, Ph), 7.21(1H, d, J = 8.18 Hz, Ph), 3.89(3H, s, CH$_3$O); IR(KBr)(cm$^{-1}$) = 3466, 3387, 3084, 3032, 3015, 2976, 2839, 1591, 1483, 1444, 1427, 1286, 1250, 1188, 1072, 1032, 997, 875, 785, 761, 684 |

TABLE 2-continued

| Exam. | aryl halide | product | Physical property data |
|---|---|---|---|
| 8 | 1-bromo-2-butoxybenzene | 4-butoxyphenyl-diphenylsulfonium bromide | yield: 78%; m.p.: 130.4-132.5° C.; $^1$H-NMR(400 MHz, CDCl$_3$) δ = 7.87(2H, d, J = 8.79 Hz, Ph), 7.80-7.68(10H, m, Ph), 7.19(2H, d, J = 9.03 Hz, Ph), 4.06(2H, t, J = 6.34 Hz, OCH$_2$), 1.79(2H,dt, J = 6.34 Hz, J = 21.49, CH$_2$), 1.49(2H, dq, J = 7.45 Hz, J = 21.49 Hz, CH$_2$), 0.97(3H, t, J = 7.45 Hz, CH$_3$); IR(KBr)(cm$^{-1}$) = 3483, 3406, 3192, 3080, 3022, 2957, 2874, 2575, 1900, 1767, 1682, 1587, 1475, 1444, 1415, 1309, 1261, 1178, 1120, 1068, 1022, 999, 964, 856, 763, 688 |
| 9 | 1-bromo-4-tert-butoxybenzene | 4-tert-butoxyphenyl-diphenylsulfonium bromide | yield: 40%; m.p.: 89.4-95.5° C.; $^1$H-NMR(400 MHz, CDCl$_3$) δ = 7.86-7.81(6H, m, Ph), 7.74-7.28(6H, m, Ph), 7.23(2H, d, J = 9.03 Hz, Ph), 1.49(9H, s, CH$_3$); IR(KBr)(cm$^{-1}$) = 3053, 2972, 2872, 1579, 1491, 1475, 1442, 1396, 1369, 1253, 1163, 1068, 997, 898, 866, 765, 744, 684 |
| 10 | 1-bromo-4-methylthio-benzene | 4-methylthiophenyl-diphenylsulfonium bromide | yield: 83%; m.p.: 160.8-161.8° C.; $^1$H-NMR(400 MHz, CDCl$_3$) δ = 7.86-7.78(6H, m, Ph), 7.76-7.69(6H, m, Ph), 7.48(2H, d, J = 8.54 Hz, Ph), 2.53(3H, s, CH$_3$S); IR(KBr)(cm$^{-1}$) = 3447, 3045, 2990, 2943, 1566, 1547, 1475, 1441, 1402, 1313, 1201, 1178, 1099, 1062, 997, 825, 804, 761, 748, 682 |
| 11 | 1-bromo-2,4,6-trimethyl-benzene | 2,4,6-trimethylphenyl-diphenylsulfonium bromide | yield: 23%; m.p.: 202.0-202.6° C.; $^1$HNMR(400 MHz, CDCl$_3$) δ = 7.80-7.76(6H, m, Ph), 7.70-7.68(4H, m, Ph), 7.23(2H, s, Ph), 2.43(3H, s, CH$_3$), 2.36(6H, s, CH$_3$); IR(KBr)(cm$^{-1}$) = 3449, 3387, 3057, 2991, 1597, 1572, 1471, 1446, 1385, 1300, 1172, 1039, 997, 879, 754, 686 |

TABLE 3

| Exam. | aryl halide | product | Physical property data |
|---|---|---|---|
| 13 | 1-bromo-4-fluorobenzene | 4-fluorophenyl-diphenylsulfonium bromide | yield: 66%; m.p.: 222.0-223.2° C.; $^1$H-NMR(400 MHz, CDCl$_3$) δ = 8.11-8.07(2H, m, Ph), 7.88-7.86(4H, m, Ph), 7.79-7.69(6H, m, Ph), 7.44-7.39(2H, m; Ph); IR(KBr)(cm$^{-1}$) = 3466, 3071, 3015, 2986, 1587, 1491, 1446, 1404, 1309, 1240, 1165, 1103, 1066, 995, 844, 815, 756, 686 |
| 14 | 1-bromo-4-chlorobenzene | 4-chlorophenyl-diphenylsulfonium bromide | yield: 66%; m.p.: 221.6-222.6° C.; $^1$H-NMR(400 MHz, CDCl$_3$) δ = 8.05-7.73(6H, m, Ph), 7.72-7.61(8H, m, Ph); IR(KBr)(cm$^{-1}$) = 3478, 3069, 3003, 2953, 1570, 1475, 1446, 1400, 1313, 1282, 1184, 1091, 1068, 1008, 997, 933, 841, 815, 754, 684 |
| 15 | 1-bromo-4-trifluoro-methylbenzene | 4-trifluoromethyl phenyldiphenyl-sulfonium bromide | yield: 72%; m.p.: 221.6-222.6° C.; $^1$H-NMR(400 MHz, CDCl$_3$) δ = 8.18(2H, d, J = 8.30 Hz, Ph), 7.96-7.94(6H, m, Ph), 7.82-7.72(6H, m, Ph); IR(KBr)(cm$^{-1}$) = 3439, 3026, 1604, 1477, 1446, 1402, 1325, 1176, 1134, 1060, 1010, 844, 752, 702, 684 |
| 16 | 1-bromo-naphthalene | 1-naphthyldi-phenylsulfonium bromide | yield: 42%; m.p.: 193.9-195.3° C.; $^1$H-NMR(400 MHz, CDCl$_3$) δ 8.37(1H, d, J = 8.06 Hz, C10H7), 8.29(1H, d, J = 8.30 Hz, C$_{10}$H$_7$), 8.07(1H, d, J = 7.81 Hz, C$_{10}$H$_7$), 7.92-7.88(4H, m, Ph),7.83-7.67(9H, m, Ph, C$_{10}$H$_7$), 7.48(1H, d, J = 7.66Hz, C$_{10}$H$_7$); IR(KBr)(cm$^{-1}$) = 3460, 3391, 3049, 1618, 1593, |

TABLE 3-continued

| Exam. | aryl halide | product | Physical property data |
|---|---|---|---|
| | | | 1504, 1475, 1446, 1367, 1346, 1323, 1290, 1265, 1165, 1070, 997, 943, 864, 806, 779, 763, 688, 661 |

Examples 17 to 23

Synthesis of Various Sulfonium Salts

The same procedure as in Example 1 was carried out except for using bromobenzene as an aryl halide instead of 4-bromotoluene used in Example 1 and the predetermined sulfoxides shown in Tables 4 and 5 as a sulfoxide instead of diphenyl sulfoxide, to obtain objective compounds. The results are shown in Table 4.

TABLE 4

| Exam. | aryl halide | product | Physical property data |
|---|---|---|---|
| 17 | bis(4-methyl-phenyl)sulfoxide | bis(4-methyl-phenyl)phenylsulfonium bromide | yield: 90%; m.p.: 207.8-208.9° C.; $^1$H-NMR(400 MHz, CDCl$_3$) δ = 7.78(2H, d, J = 7.81 Hz, Ph), 7.73-7.68(7H, m, Ph), 7.48(4H, d, J = 8.55 Hz, Ph), 2.45(6H, S, CH$_3$); IR(KBr)(cm$^{-1}$) = 3617, 3065, 3003, 2955, 1589, 1491, 1443, 1402, 1315, 1290, 1186, 1124, 1068, 1014, 825, 806, 760, 688 |
| 18 | bis(4-methoxy-phenyl)sulfoxide | bis(4-methoxy-phenyl)phenylsulfonium bromide | yield: 94%; colorless oily substance; $^1$H-NMR(400 MHz, CDCl$_3$) δ = 7.81(4H, d, J = 8.79 Hz, Ph), 7.72-7.69(5H, m, Ph), 7.20(4H, D, J = 8.79 Hz, Ph), 3.90(6H, s, OCH$_3$); IR(KBr)(cm$^{-1}$) = 3400, 3086, 2976, 2841, 2575, 1589, 1495, 1445, 1416, 1311, 1271, 1180, 1126, 1076, 1018, 837, 798, 752, 686 |
| 19 | bis(4-tert-butyl-phenyl)sulfoxide | bis(4-tert-butyl-phenylsulfonium bromide | yield: 91%; m.p.: 245.6-245.9° C.; $^1$H-NMR(400 MHz, CDCl$_3$) δ = 7.86-7.82(6H, m, Ph), 7.76-7.71(7H, m, Ph), 1.35(9H, s, CH$_3$); IR(KBr)(cm$^{-1}$) = 3067, 2964, 2872, 1587, 1493, 1471, 1446, 1400, 1363, 1269, 1203, 1117, 1072, 1009, 997, 850, 837, 767, 690 |
| 20 | bis(4-trifluoromethyl-phenyl)sulfoxide | bis(4-trifluoromethyl-phenyl)phenylsulfonium bromide | yield: 39%; m.p.: 283.9-284.8° C.; $^1$H-NMR(400 MHz, CDCl$_3$) δ = 7.87-7.85(6H, m, Ph), 7.81-7.04(7H, m, Ph); IR(KBr)(cm$^{-1}$) = 3073, 3046, 2985, 1578, 1477, 1447, 1327, 1138, 1062, 995, 837, 769, 750, 684 |
| 21 | bis(4-fluoro-phenyl)sulfoxide | bis(4-fluoro-phenyl)phenylsulfonium bromide | yield: 72%; m.p.: 241.6-242.1° C.; $^1$H-NMR(400 MHz, CDCl$_3$) 6 32 8.13-8.09(4H, m, Ph), 7.89-7.86(2H, m, Ph), 7.79-7.70(3H, m, Ph), 7.46-7.41(4H, m, Ph); IR(KBr)(cm$^{-1}$) = 3574, 3480, 3090, 3047, 3018, 2976, 1585, 1491, 1448, 1408, 1300, 1240, 1163, 1105, 1070, 1008, 848, 814, 756, 686 |
| 22 | bis(4-chloro-phenyl)sulfoxide | bis(4-chloro-phenyl)phenylsulfonium bromide | yield: 66%; m.p.: 179.3-180.4° C.; $^1$H-NMR(400 MHz, CDCl$_3$) δ = 8.02-7.98(3H, m, Ph), 7.92-7.76(2H, m, Ph), 7.75-7.65(8H, m, Ph); IR(KBr)(cm$^{-1}$) = 3069, 2984, 1570, 1475, 1446, 1394, 1309, 1157, 1039, 1064, 997, 829, 769, 746, 686 |
| 23 | bis(4-hydroxy-phenyl)sulfoxide | bis(4-hydroxy-phenyl)phenylsulfonium | yield: 69%; m.p.: 252.6-253.0° C.; $^1$H-NMR(400 MHz, CDCl$_3$) δ = 7.80-7.70(3H, m, Ph), 7.64-7.62(6H, m, Ph), 7.13-7.10(4H, m, Ph), 3.30 3.29(2H, brd, OH); IR(KBr)(cm$^{-1}$) = 3061, 1595, 1579, 1496, 1441, 1342, 1288, 1224, 1109, 1072, 846, 744, 719, 679 |

Formation rate of byproducts in Examples 1 to 23 was measured using high-speed liquid chromatography [Wavelength: 237 nm, Flow rate: 0.75 ml/min, Mobile phase: 6 mM tetrapropylammonium hydroxide (TPAH) solution in water-acetonitrile (water/acetonitrile=13/7) (pH 7.0), Measuring time: 30 min]. There was no formation of byproducts.

Comparative Example 1 and Experimental Examples 1 to 6

Effect of the Equivalent of an Activator Relating to the Present Invention

The same procedure as in Example 1 was carried out except for using TMSCl (5 equiv.) used in Example 1 in the various equivalents shown in the following Table 5, to obtain objective 4-methylphenyldiphenylsulfonium bromide. Yields of the obtained objective compound, triphenylsulfonium bromide (byproduct 1) and bis(4-methylphenyl)phenyl sulfonium bromide (byproduct 2) are shown in Table 5.

TABLE 5

| | Grignard reagent/ Diphenylsulfoxide (equiv.) | TMSCl/ Diphenylsulfoxide (equiv.) | Objective Compound (%) | Byproduct 1 (%) | Byproduct 2 (%) |
|---|---|---|---|---|---|
| Comparative Example 1 | 2.5 | 2.5 | 59 | 3 | 2 |
| Experimental Example 1 | 2.5 | 3.0 | 72 | 2 | 1 |
| Experimental Example 2 | 2.5 | 4.0 | 72 | 1 | — |
| Experimental Example 3 (Example 1) | 2.5 | 5.0 | 76 | — | — |
| Experimental Example 4 | 2.5 | 6.0 | 68 | — | — |
| Experimental Example 5 | 2.5 | 7.0 | 70 | — | — |
| Experimental Example 6 | 2.5 | 7.5 | 70 | — | — |

As is clear from the comparison of the result of Comparative Example 1 and Experimental Examples 1 to 6 in Table 5, it can be understood that the yield of the objective compound is high with byproduct formation rates being extremely low in Experimental Examples 1 to 6, while the yield of the objective compound is low with byproducts being formed in Comparative Example 1. In particular, it can be also understood that byproducts are not formed at all in Experimental Examples 3 to 6.

It can be understood from the above results that byproduct formation is controlled by using an activator relating to the present invention of usually 3 to 7.5 equivalents, preferably 4 to 7 equivalents and more preferably 4.5 to 6 equivalents, relative to 1 equivalent of the diaryl sulfoxide.

INDUSTRIAL APPLICABILITY

The method for producing a triarylsulfonium salt, of the present invention can efficiently produce a desired sulfonium salt in a high yield by using a larger amount of an activator with high affinity for an oxygen atom than that conventionally used, without having such problems as severe reaction conditions under high temperature (e.g. reflux operation by heating, melt reaction, etc.), generation of sulfurous acid gas, drainage of a large amount of aluminum waste liquid, production of a sulfonium salt alone having the same three aromatic rings on the cation portion and formation of byproducts as impurities. Such effects are obtained by greatly increasing an amount of use of an activator with high affinity for an oxygen atom, which has not been predicted at all.

The invention claimed is:

1. A method for producing a triarylsulfonium salt represented by the general formula [4]:

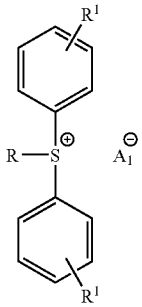

[4]

wherein, the two $R^1$'s are the same and are hydrogen atom, halogen atom, alkyl group, haloalkyl group having 1 to 4 carbon atoms, alkoxy group, acyl group, hydroxyl group, amino group, nitro group or cyano group; R represents an aryl group which may have a substituent selected from a halogen atom, an alkyl group, a haloalkyl group having 1 to 4 carbon atoms, an alkoxy group, an alkylthio group, a N-alkylcarbamoyl group and a carbamoyl group, with the proviso that R is different from

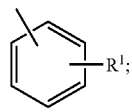

and $A_1$ represents a strong acid residue,
comprising reacting a diaryl sulfoxide represented by the general formula [1]:

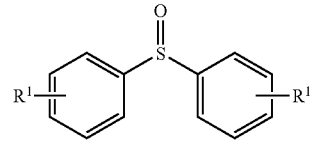

[1]

and an aryl Grignard reagent represented by the general formula [2]:

$$RMgX \qquad [2]$$

wherein, X represents a halogen atom; R represents the same as above,
in the presence of an activator with high affinity for oxygen of 6.0 to 7.5 equivalents relative to the above diaryl sulfoxide, and then reacting the resultant reaction mixture with a strong acid represented by the general formula [3]:

$$HA_1 \qquad [3]$$

wherein, $A_1$ represents the same as above,
or a salt thereof.

2. The method according to claim 1, wherein the activator with high affinity for oxygen is a halogenotriorganosilane.

3. The method according to claim 1, wherein the activator with high affinity for oxygen is a halogenotrialkylsilane.

4. The method according to claim 1, wherein the activator with high affinity for oxygen is chlorotrimethylsilane.

5. The method according to claim 1, wherein the amount of use of an activator with high affinity for oxygen is 1.2 to 3 equivalents relative to the aryl Grignard reagent represented by the general formula [2].

6. The method according to claim 1, wherein a strong acid residue represented by $A_1$ is an anion derived from a hydrohalic acid represented by the general formula [5]:

$$HX_1 \qquad [5]$$

wherein, $X_1$ represents a halogen atom,
a sulfonic acid represented by the general formula [6]:

$$R^2\text{---}SO_3H \qquad [6]$$

wherein, $R^2$ represents an alkyl group, an aryl group or an aralkyl group, which may have a halogen atom, or a camphor group,
or an inorganic strong acid represented by the general formula [7]:

$$HM_1Fn \qquad [7]$$

wherein, $M_1$ represents a metalloid atom; and n represents 4 or 6.

7. The method according to claim 6, wherein $X_1$ is a chlorine atom or a bromine atom.

8. The method according to claim 6, wherein the metalloid atom represented by $M_1$ is a boron atom, a phosphorus atom, an arsenic atom or an antimony atom.

9. The method according to claim 1, wherein the reaction of the diaryl sulfoxide and the aryl Grignard reagent is conducted in the presence of the activator of 6.0 to 7.5 equivalents relative the diaryl sulfoxide.

* * * * *